(12) United States Patent
Vitzthum et al.

US009469687B2

(10) Patent No.: US 9,469,687 B2
(45) Date of Patent: Oct. 18, 2016

(54) BINDING PARTNERS OF THE PLACENTAL GROWTH FACTOR, ESPECIALLY ANTIBODIES DIRECTED AGAINST THE PLACENTAL GROWTH FACTOR, AND PRODUCTION AND USE THEREOF

(71) Applicant: SIEMENS HEALTHCARE DIAGNOSTICS PRODUCTS GMBH, Marburg (DE)

(72) Inventors: Frank Vitzthum, Lahntal-Sterzhausen (DE); Stefan Teigelkamp, Niederwalgern (DE); Harald Althaus, Wetter (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 14/727,568

(22) Filed: Jun. 1, 2015

(65) Prior Publication Data
US 2015/0299308 A1 Oct. 22, 2015

Related U.S. Application Data

(63) Continuation of application No. 11/920,160, filed as application No. PCT/EP2006/004278 on May 8, 2006.

(30) Foreign Application Priority Data

May 9, 2005 (DE) ........................ 10 2005 022 047

(51) Int. Cl.
| *C07K 16/22* | (2006.01) |
| *C07K 14/515* | (2006.01) |
| *C12N 5/20* | (2006.01) |
| *G01N 33/74* | (2006.01) |
| *G01N 33/531* | (2006.01) |
| *G01N 33/574* | (2006.01) |
| *C12N 5/16* | (2006.01) |

(52) U.S. Cl.
CPC ............. *C07K 16/22* (2013.01); *C07K 14/515* (2013.01); *C12N 5/163* (2013.01); *G01N 33/531* (2013.01); *G01N 33/74* (2013.01); *C07K 2317/14* (2013.01); *C07K 2317/34* (2013.01); *C07K 2319/30* (2013.01); *G01N 33/57488* (2013.01); *G01N 2333/515* (2013.01)

(58) Field of Classification Search
CPC C07K 14/515; C07K 16/22; C07K 2317/14; C07K 2317/34; C07K 2319/30; G01N 33/74; G01N 33/531; G01N 33/536; G01N 33/543; G01N 33/566; G01N 33/574; G01N 33/57488; G01N 2333/515; G01N 2800/22; C12N 5/20
See application file for complete search history.

(56) References Cited

U.S. PATENT DOCUMENTS

| 3,996,345 | A | 12/1976 | Ullman et al. |
| 4,448,908 | A | 5/1984 | Pauly et al. |
| 4,563,431 | A | 1/1986 | Pauly et al. |
| 4,945,146 | A | 7/1990 | Kapmeyer et al. |
| 4,962,046 | A | 10/1990 | Kapmeyer |
| 5,340,716 | A | 8/1994 | Ullman et al. |
| 5,501,969 | A | 3/1996 | Hastings et al. |
| 5,545,834 | A | 8/1996 | Singh et al. |
| 5,919,899 | A | 7/1999 | Persico et al. |
| 6,346,381 | B1 | 2/2002 | Cohen et al. |
| 6,361,946 | B1 | 3/2002 | Alitalo |
| 7,863,239 | B2 | 1/2011 | Timmerman et al. |
| 2003/0194704 | A1 | 10/2003 | Penn et al. |
| 2004/0126828 | A1 | 7/2004 | Karumanchi et al. |
| 2007/0111326 | A1 | 5/2007 | Sogin et al. |

FOREIGN PATENT DOCUMENTS

| EP | 0080614 | 6/1983 |
| EP | 0227054 | 7/1987 |
| EP | 0246446 | 12/1990 |
| EP | 0411945 A2 | 2/1991 |
| EP | 0515194 A2 | 11/1992 |
| WO | WO 92/06194 | 4/1992 |
| WO | WO 95/06877 | 3/1995 |
| WO | WO 99/24056 | 5/1999 |
| WO | WO 95/25172 | 9/1999 |
| WO | WO 00/75163 A1 | 12/2000 |
| WO | WO 01/85796 | 4/2002 |
| WO | WO 03/097688 A2 | 11/2003 |
| WO | WO 2005/077007 | 8/2005 |
| WO | WO 2005/124353 | 12/2005 |
| WO | WO 2006/267693 | 3/2006 |
| WO | WO 2006/078161 A1 | 7/2006 |

OTHER PUBLICATIONS

Heeschen et al., Prognostic Value of Placental Growth Factor in Patients With Acute Chest Pain, *JAMA* 291:435-41 (2004).
International Preliminary Report of Patentability for PCT/EP2006/004278, dated Apr. 2, 2007.
International Search Report for PCT/EP/004278, mailed Aug. 29, 2008.
Iyer et al., The Crystal Structure of Human Placenta Growth Factor-1 (PIGF-1), an Angiogenic Protein, at 2.0 Å Resolution, *J. Biol. Chem.* 276:12153-61 (2001).
Iyer et al. Role of Placenta Growth Factor in Cardiovascular Health, Trends Cardiovasc Med 12:128-34 (2002).
Maynard et al. Excess Placental Soluble Fms-Like Tyrosine Kinase 1 (Sflt1) May Contribute to Endothelial Dysfunction, Hypertension, and Proteinuria in Preeclampsia, Journal of Clinical Invest. 111:649-658 (2003).
R&D Systems Catalog No. AF-264-PB or DPG00 Product Descriptions.

(Continued)

*Primary Examiner* — Gail R Gabel
(74) *Attorney, Agent, or Firm* — Finnegan Henderson Farabow Garrett & Dunner LLP

(57) ABSTRACT

The invention relates to binding partners of the placental growth factor (or placenta growth factor, PIGF), especially antibodies directed against the placental growth factor, and production and use thereof.

7 Claims, No Drawings

(56) References Cited

OTHER PUBLICATIONS

Tam, Synthetic Peptide Vaccine Design: Synthesis and Properties of a High-Density Multiple Antigenic Peptide System, Proc. Natl. Acad. Sci. USA 85:5409-5413 (1988).

Yang et al. Evidence of a Novel Isoform of Placenta Growth Factor (PIGF-4) Expressed in Human Trophoblast and Endothelial Cells, J. Reprod Immunol 60:53-60 (2003).

Christinger H.W. et al., Protein Structure and Folding: The Crystal Structure of Placental Growth Factor in Complex with Domain 2 of Vascular Endothelial Growth Factor Receptor-1, J. Biol. Chem. 279:10382-10388 (2004).

Park et al., Placental Growth Factor, J. Biol. Chem. 269: 25646-25654 (1994).

Perisco et al., Structure, Expression and Receptor-Binding Properties of Placental Growth Factor (PIGF), Curr. Top. Microbiol. Immunol, 237: 31-40 (1999).

Maglione et al., Isolation of a Human Placenta cDNA Coding for a Protein Related to the Vascular Permeability Factor, PNAS 88: 9267-9271 (1991).

Fischer et al., Anti-PIGF Inhibits Growth of VEGF(R)-Inhibitor-Resistant Tumors Without Affecting Healthy Vessels, Cell 131: 463-475 and supplement (2007).

Cao et al., Heterodimers of Placenta Growth Factor/Vascular Endothelial Growth Factor, J. Biol. Chem. 271: 3154-3162 (1996).

Harlow et al., Antibodies, A Laboratory Manual, Cold Spring Harbor Laboratory, Cold Spring Harbor, 72-77 (1988).

Hellstrom et al., In Monoclonal Antibodies for Cancer Detection and Therapy (Baldwin et al. eds.), Academic Press, London 20 (1985).

Mamluk et al., Neuropilin-1 Binds Vascular Endothelial Growth Factor 165, Placental Growth Factor-2, and Heparin Via its b1b2 Domain, J. Biol. Chem. 277: 24818-24825 (2002).

Cao et al., Placenta Growth Factor: Identification and Characterization of a Novel Isoform Generated by RNA Alternative Splicing, Biochem. Biophys. Res. Comm. 235: 493-498 (1997).

Errico et al., Identification of Placenta Growth Factor Determinants for Binding and Activation of Flt-1 Receptor, J. Biol. Chem. 279: 43929-43939 (2004).

Migdal et al., Neuropilin-1 is a Placenta Growth Factor-2 Receptor, J. Biol. Chem. 273: 22272-22278 (1998).

Sawano et al., Flt-1 But Not KDR/Flk-1 Tyrosine Kinase is a Receptor for Placenta Growth Factor, Which is Related to Vascular Endothelial Growth Factor, Cell Growth & Differentiation 7: 213-221 (1996).

Non-final Office Action issued in U.S. Appl. No. 11/920,160 dated Mar. 26, 2010.

Final Office Action issued in U.S. Appl. No. 11/920,160 dated Dec. 8, 2010.

Non-final Office Action issued in U.S. Appl. No. 11/920,160 dated Mar. 25, 2014.

Non-final Office Action issued in U.S. Appl. No. 11/920,160 dated Aug. 8, 2014.

Non-final Office Action issued in U.S. Appl. No. 11/920,160 dated Dec. 9, 2014.

Office Action issued in U.S. Appl. No. 11/920,160 dated Mar. 19, 2015.

Hauser, S. et al., "A Heparin-Binding Form of Placenta Growth Factor (PIGF-2) is Expressed in Human Umbilical Vein Endothelial Cells and in Placenta," *Growth Factor*, 9:259-268, (1993).

BINDING PARTNERS OF THE PLACENTAL GROWTH FACTOR, ESPECIALLY ANTIBODIES DIRECTED AGAINST THE PLACENTAL GROWTH FACTOR, AND PRODUCTION AND USE THEREOF

PRIOR APPLICATIONS

This application a continuation of application Ser. No. 11/920,160, filed Nov. 9, 2007, which is a 35 U.S.C. §371 National Phase Entry application of International Application PCT/EP2006/004278, filed May 8, 2006, which designated the U.S. and which claims the benefit under 35 U.S.C. §119 of German Application No. 10 2005 022 047.9, filed May 9, 2005, the entire contents of which are hereby incorporated by reference.

FIELD OF THE INVENTION

The invention relates to binding partners of the placental growth factor (or placenta growth factor, PlGF), especially antibodies directed against the placental growth factor, and production and use thereof.

BACKGROUND OF THE INVENTION

PlGF is involved in important physiological and pathological processes, in particular angiogenesis. It plays an important part in tumor progression, kidney diseases, which are caused in particular by diabetes mellitus, in psoriasis, inflammatory diseases, in particular rheumatoid arthritis, in cardiovascular diseases and the like [Iyer, S.; Leonidas, D. D.; Swaminathan, G. J.; Maglione, D.; Battisti, M.; Tucci, M.; Persico, M. G.; Acharya, K. R. *J Biol Chem* 2001, 276, (15), 12153-61./Iyer, S.; Acharya, K. R. *Trends Cardiovasc Med* 2002, 12, (3), 128-34./Heeschen, C.; Dimmeler, S.; Fichtlscherer, S.; Hamm, C. W.; Berger, J.; Simoons, M. L.; Zeiher, A. M. *JAMA* 2004, 291, (4), 435-41./Yang, W.; Ahn, H.; Hinrichs, M.; Torry, R. J.; Torry, D. S. *J Reprod Immunol* 2003, 60, (1), 53-60.].

PlGF is mainly expressed in the placenta and belongs to the "cysteine-knot" protein family. PlGF occurs in different forms. Different forms of PlGF are (I) primary isoforms and (II) secondary isoforms. (III) In addition, a distinction can be made between free PlGF (fPlGF) and bound PlGF (gPlGF).

(I) Primary PlGF Isoforms

Primary PlGF isoforms are characterized by the primary sequence, i.e. the order of the amino acids in the protein. Alternative splicing and posttranslational modifications, such as glycosylations, phosphorylations, degradation (degradation products, fragments, etc.), acetylations etc., lead to different primary PlGF isoforms. To date, four different primary isoforms of human PlGF, PlGF-1 (PlGF-131), PlGF-2 (PlGF152), PlGF-3 (PlGF-203) and PlGF-4 have been described.

The sequence of the PlGF-1 precursor (Sequence number (SN) 1V) is as follows:

```
SN 1V
                                                          (SEQ ID NO: 1)
   1 MPVMRLFPCF LQLLAGLALP AVPPQQWALS AGNGSSEVEV VPFQEVWGRS YCRALERLVD

61 VVSEYPSEVE HMFSPSCVSL LRCTGCCGDE NLHCVPVETA NVTMQLLKIR SGDRPSYVEL

121 TFSQHVRCEC RPLREKMKPE RCGDAVPRR
```

Secreted PlGF-1 does not as a rule possess the leader sequence of the PlGF-1 precursor (PlGF precursor) and thus begins at the N-terminus with alanine (A) (stated as A in the sequence of the PlGF-1 precursor, see above). This as a rule applies also to the other primary PlGF isoforms.

The sequence of the primary PlGF-1 isoform is thus as follows:

```
SN 1:
                                                          (SEQ ID NO: 2)
   1 ALPAVPPQQW ALSAGNGSSE VEVVPFQEVW GRSYCRALER LVDVVSEYPS EVEHMFSPSC

61 VSLLRCTGCC GDENLHCVPV ETANVTMQLL KIRSGDRPSY VELTFSQHVR CECRPLREKM

121 KPERCGDAVP RR
```

In this primary sequence, possible sites for post-translational modifications, and hence also the presence of post-translationally modified primary isoforms, can be discerned. For example, in general in vivo the posttranslationally modified primary PlGF isoform of PlGF-1 glycosylated at position 84 (asparagine, N) is present.

As the first N-terminal amino acid of the primary isoform PlGF-1, methionine (M) is often stated instead of alanine. This in general relates to recombinantly, for example in *Escherichia coli* (*E. coli*), expressed PlGF-1(rPlGF-1), and in particular to the human rPlGF-1 (rhPlGF-1). Here AUG, which codes for methionine, is used as the start codon. Such a PlGF expressed in *E. coli* has no posttranslational modifications, in particular also no glycosylations.

The sequence of the recombinant, human, primary PlGF-1 isoform is generally stated as follows:

SN 1RH:

```
                                                          (SEQ ID NO: 3)
  1 MLPAVPPQQW ALSAGNGSSE VEVVPFQEVW GRSYSRALER LVDVVSEYPS EVEHMFSPSC

61 VSLLRCTGCC GDENLHCVPV ETANVTMQLL KIRSGDRPSY VELTFSQHVR CECRPLREKM

121 KPERCGDAVP RR
```

Through alternative splicing, the sequence RRRPKGRG-KRRREKQRPTDCHL (SEQ ID NO: 64) is present in the PlGF-2 isoform instead of the arginine (R) 124. The sequence of the primary PlGF-2 isoform thus reads:

SN 2:

```
                                                          (SEQ ID NO: 4)
  1 ALPAVPPQQW ALSAGNGSSE VEVVPFQEVW GRSYCRALER
    LVDVVSEYPS EVEHMFSPSC

61 VSLLRCTGCC GDENLHCVPV ETANVTMQLL KIRSGDRPSY
    VELTFSQHVR CECRPLREKM

121 KPERRRPKGR GKRRREKQRP TDCHLCGDAV PRR
```

An insert of 72 amino acids inserted by alternative splicing (HSPGRQSPDMPGDFRADAPSFLPPRRSLPM-LFRMEWGCALTGSQS AVWPSSPVPEEIPRMH-PGRNGKKQQRK (SEQ ID NO: 65)) leads to the sequence of the primary PlGF-3 isoform:

SN 3:

```
                                                          (SEQ ID NO: 5)
  1 ALPAVPPQQW ALSAGNGSSE VEVVPFQEVW GRSYCRALER LVDVVSEYPS EVEHMFSPSC

61 VSLLRCTGCC GDENLHCVPV ETANVTMQLL KIRSGDRPSY VELTFSQHVR CECRHSPGRQ

121 SPDMPGDFRA DAPSFLPPRR SLPMLFRMEW GCALTGSQSA VWPSSPVPEE IPRMHPGRNG

181 KKQQRKPLRE KMKPERCGDA VPRR
```

The primary PlGF-4 isoform contains sequences both of the PlGF-2 isoform (italic) and also of the PlGF-3 isoform (underlined):

SN 4:

```
                                                          (SEQ ID NO: 6)
  1 ALPAVPPQQW ALSAGNGSSE VEVVPFQEVW GRSYCRALER LVDVVSEYPS EVEHMFSPSC

61 VSLLRCTGCC GDENLHCVPV ETANVTMQLL KIRSGDRPSY VELTFSQHVR CECRHSPGRQ

121 SPDMPGDFRA DAPSFLPPRR SLPMLFRMEW GCALTGSQSA VWPSSPVPEE IPRMHPGRNG

181 KKQQRKPLRE KMKPERRRPK GRGKRRREKQ RPTDCHLCGD AVPRR
```

(II) Secondary PlGF Isoforms

Secondary PlGF isoforms result from the combination of primary PlGF isoforms or other molecules, in particular molecules which are homologous to PlGF. The primary PlGF isoforms or other molecules are subunits of the secondary PlGF isoforms. In general, secondary PlGF isoforms consist of two subunits. Thus PlGF is as a rule present as a dimer, i.e. as a homodimer or a heterodimer. Homodimers consist of two identical primary PlGF isoforms (sub-units) such as PlGF-1×PlGF-1, PlGF-2×PlGF-2, PlGF-3×PlGF-3 and PlGF-4×PlGF-4. Heterodimers consist of two different primary PlGF isoforms or of one primary PlGF isoform and one other molecule, in particular a PlGF homolog such as vascular endothelial growth factor (VEGF) and primary isoforms thereof. Possible examples of heterodimers are PlGF-1×PlGF-2, PlGF-3×PlGF-4, PlGF-1×VEGF, etc.

(III) Free PlGF (fPlGF) and Bound PlGF (gPlGF)

Since PlGF forms complexes with binding partners, the complexed or bound forms of PlGF must also be considered as well as the isoforms. In principle, the free primary, but in particular the free secondary PlGF isoforms (free PlGF, fPlGF), should be distinguished from the complexed or bound forms (bound PlGF, gPlGF). gPlGF is for example homodimeric PlGF-1 which is present in complexed form. These can be simple complexes, i.e. a PlGF-1 homodimer is bound to a receptor, for example the membrane-bound fms-like tyrosine kinase receptor-1 (mFlt-1). Other examples are complexes with the soluble Flt-1 (sFlt-1), with neurophilins (NP; in particular NP-1 and NP-2), with the kinase domain-containing receptor/fetal liver kinase receptor (KDR/Flk-1, VEGFR-2), with heparin sulfate proteoglycans (HSPG) and isoforms, homologs, fragments and degradation products thereof. Multilayer constituted complexes of several and sometimes different PlGF isoforms and several and sometimes different binding partners, in particular receptors, are also possible.

The function of PlGF is mediated, modulated or inhibited by binding to the membrane-bound or soluble fms-like tyrosine kinase receptor-1 (fms-like tyrosine kinase receptor-1 (Flt-1) or Vascular Endothelial Growth Factor (VEGF) receptor-1 (VEGFR-1)) and the kinase domain-containing receptor/fetal liver kinase receptor (KDR/Flk-1 or VEGFR-2). In addition to other possible functions of PlGF, the binding of PlGF to membrane-bound Flt-1 (mFlt-1) is especially important. This results in mFlt-1 transphosphorylation and thus activates signal transduction cascades [Iyer, S.; Acharya, K. R. *Trends Cardiovasc Med* 2002, 12, (3), 128-34.].

In contrast to this, it is presumed that the binding of PlGF to soluble Flt-1 (sFlt-1) serves to reduce the physiological activity of PlGF [Iyer, S.; Acharya, K. R. *Trends Cardiovasc Med* 2002, 12, (3), 128-34.]. Furthermore it is presumed that the PlGF isoform is involved. PlGF-2, which is possibly linked to the membrane, has a cationic insert of 21 amino acids at the carboxy terminal end. Through the binding of anionic, in particular polyanionic, substances such as heparin, heparin sulfate proteoglycans, etc., further functions can be mediated. The N-glycosylation of asparagine (Asn) 84 and the amino acid sequence which is present in PlGF-3 can also have similar effects. Moreover, it is presumed that the binding of PlGF and VEGF has yet another effect, since here the VEGF expression and thus its activity is negatively regulated [Iyer, S.; Acharya, K. R. *Trends Cardiovasc Med* 2002, 12, (3), 128-34.]. In summary, this means that the various forms of PlGF have different functions or exert different effects.

For the current detection methods and binding partners, in particular antibodies, which are at present used for analytical and diagnostic purposes, there is the problem that the different forms of PlGF are not, or not efficiently enough (not sufficiently specifically) distinguished. For example, the "Anti-human PlGF Antibody" from R&D Systems, Inc. does not exclusively recognize certain PlGF forms, in particular rhPlGF-1 homodimer but also the heterodimer of rhPlGF and VEGF and rhPlGF-2 (R&D Systems Catalog Number: AF-264-PB or DPG00 product descriptions).

Furthermore, fPlGF or gPlGF are not exclusively detected, i.e. with the existing antibodies, a distinction between fPlGF and gPlGF is not or not sufficiently efficiently made. In particular, the specific detection of fPlGF is inadequate. This is demonstrated by the fact that rhFlt-1 in the form of rhFlt-1/Fc has an effect on the determination of PlGF (R&D Systems Catalog Number: DPG00). This non-specificity is confirmed in the literature [Maynard, S. E.; Min, J. Y.; Merchan, J.; Lim, K. H.; Li, J.; Mondal, S.; Libermann, T. A.; Morgan, J. P.; Sellke, F. W.; Stillman, I. E.; Epstein, F. H.; Sukhatme, V. P.; Karumanchi, S. A. *J Clin Invest* 2003, 111, (5), 649-58.]. Maynard et al. show that the relevant R&D Systems ELISA (R&D Systems Catalog Number: AF-264-PB or DPG00) does show a certain specificity for fPlGF, however the studies performed show that this specificity is low. In the determination of 0.5 ng/mL rhPlGF-1, a signal reduction of only about 12% is to be seen in the presence of 0.5 ng/mL sFlt-1. Even with a 10-fold excess of sFlt-1 (5 ng/mL), there was only a signal reduction by the factor of 2. A more pronounced signal reduction would occur with higher specificity of the antibodies used towards fPlGF.

SUMMARY OF THE INVENTION

The purpose of the present invention was thus to provide processes or components which enable the specific detection of particular PlGF forms, in particular by means of specific binding partners, in particular antibodies.

The solution of this problem consists in the provision of the objects and processes according to the invention described in the claims.

In particular, the purpose is achieved by the provision of binding partners, in particular antibodies, which bind specifically to the primary isoforms of PlGF. These binding partners, in particular antibodies, form the basis for the immunological detection and the quantification of the primary and secondary isoforms and of the free or bound PlGF forms. This applies in particular to biological materials, in particular plasma samples, for diagnostic applications. Therapeutic applications are likewise possible.

Surprisingly, the different forms of PlGF can be detected as described below. The selection of binding partners and of substances for the preparation of specific binding partners for the specific detection of free PlGF is described in more detail below:

According to the invention, specific binding partners, in particular antibodies and proteins of the receptor tyrosine kinase family, in particular Flt-1, Flt-2, Flt-3, Flt-4, preferably Flt-1, homologs, fragments and degradation products, which bind in the region of the receptor-binding domains at the poles of the secondary PlGF isoforms are especially suitable for the detection of fPlGF, in particular of non-m/sFlt-1-bound PlGF.

Especially suitable are specific binding partners, in particular antibodies which are prepared with the use of free primary and secondary PlGF isoforms, in particular secondary PlGF isoforms, preferably PlGF homodimers, particularly preferably PlGF-1 homodimer, in particular rhPlGF-1 homodimer, preferably N-glycosylated rhPlGF-1 homodimer, for example by immunizations, and which on characterization show that interactions in the region of the receptor binding site are entered into or are necessary during binding.

The "head-to-tail" orientation of the monomers (primary PlGF isoforms) in dimers (secondary PlGF isoforms) has the effect that each receptor-binding domain is situated at the poles of the PlGF dimers. The receptor binding takes place at the monomer-monomer boundary and not exclusively on one monomer.

In particular, surprisingly, peptides which only possess the sequence information of one monomer and hence do not include the whole receptor-binding domain, which is made up of both monomers, are especially suitable as immunization antigens for the production of fPlGF-specific antibodies.

Peptides which contain amino acids which are important for receptor interactions or peptides which cover sequence regions in the vicinity thereof are especially suitable as immunization antigens. The amino acids which are particularly but not exclusively important for the Flt-1 receptor interactions are shown underlined below within the PlGF-1 sequence. The PlGF-1 sequence was selected by way of example for illustration. These amino acids are also important for receptor interactions in the case of the other PlGF isoforms. The following amino acid is disclosed as SEQ ID NO: 2.

```
SN 1:
                                                                    (SEQ ID NO: 2)
  1 ALPAVPPQQW ALSAGNGSSE VEVVPFQEVW GRSYCRALER LVDVVSEYPS EVEHMFSPSC

61 VSLLRCTGCC GDENLHCVPV ETANVTMQLL KIRSGDRPSY VELTFSQHVR CECRPLREKM

121 KPERCGDAVP RR
```

E-112 and P-115, but in particular P-115, which probably play a secondary or indeed no part in the corresponding receptor interactions in the case of PlGF-3 and PlGF-4, represent an exception, since the insert of 72 amino acids (SN 3 and SN 4) described above lies between these amino acids.

The following peptides are especially suitable as immunization antigens for the preparation of fPlGF-specific antibodies (Immunization antigen numbers (IAN) 1-4):

```
IAN 1:
                                  (SEQ ID NO: 7)
SAGNGSSEVE VVPFQEVWGR SYCRALERLV

IAN 2:
                                  (SEQ ID NO: 26)
LRCTGCCGDE NLHCVPVET

IAN 3:
                                  (SEQ ID NO: 33)
VETANVTMQL LKIRSGDRP SYVELTFSQH

IAN 4:
                                  (SEQ ID NO: 66)
TFSQHVRCEC RPLREKMKPE RCGDAVPRR
```

Immunization antigens can also contain sequences from different peptides with the immunization antigen numbers IAN 1-4. For example, the following peptide can be used:

```
IAN 2/3:
                                  (SEQ ID NO: 43)
VPVETANVTM QL
```

Particular embodiments are explained in more detail below.

DETAILED DESCRIPTION OF THE INVENTION

An object of this invention are peptides consisting of 4 to 30 amino acids, preferably 5 to 20 amino acids, quite particularly preferably 10 to 15 amino acids, which are characterized in that they contain the amino acid sequences FQEVWGRSY (IAN: 1-1) (SEQ ID NO: 8), SAGNGSSEV-EVV (IAN: 1-1-1) (SEQ ID NO: 9), VVPFQEVWGRSY (IAN: 1-1-2) (SEQ ID NO: 11), GDENL (IAN: 2-1) (SEQ ID NO: 27), GCCGDENLH (IAN: 2-1-1) (SEQ ID NO: 28), QLLKIRSGDRPSY (IAN: 3-1) (SEQ ID NO: 34), QLLKI (IAN: 3-2) (SEQ ID NO: 35), RPSYV (IAN: 3-3) (SEQ ID NO: 36), RSGDRPSYVELT (IAN: 3-3-1) (SEQ ID NO: 37) and/or ECRP (IAN: 4-1) (SEQ ID NO: 46).

Peptides which contain 5 consecutive amino acids of the stated sequences, i.e. for example EVVPF (IAN: 1-2) (SEQ ID NO: 13), VVPFQ (IAN: 1-3) (SEQ ID NO: 14), VPFQE (IAN: 1-4) (SEQ ID NO: 15), PFQEV (IAN: 1-5) (SEQ ID NO: 16), FQEVW (IAN: 1-6) (SEQ ID NO: 17), QEVWG (IAN: 1-7) (SEQ ID NO: 18), EVWGR (IAN: 1-8) (SEQ ID NO: 19), VWGRS (IAN: 1-9) (SEQ ID NO: 20), WGRSY (IAN: 1-10) (SEQ ID NO: 21), GRSYC (IAN: 1-11) (SEQ ID NO: 22), RSYCR (IAN: 1-12) (SEQ ID NO: 23), SYCRA (IAN: 1-13) (SEQ ID NO: 24), YCRAL (IAN: 1-14) (SEQ ID NO: 25) or GCCGD (IAN: 2-2) (SEQ ID NO: 30), CCGDE (IAN: 2-3) (SEQ ID NO: 31), CGDEN (IAN: 2-4) (SEQ ID NO: 32), etc. down to PLREK (IAN: 4-2) (SEQ ID NO: 47), are also particularly preferable.

Immunization antigens can be used for the immunization unbound and/or carrier-bound. In order to facilitate coupling to typical carriers, for example proteins, such as ovalbumin, albumin or keyhole limpet hemocyanin, peptides which contain a lysine are preferably synthesized. The following peptides are particularly suitable for this: SAGNGSSEVEVVK (IAN: 1-1-1K) (SEQ ID NO: 10), SGDRPSYVELTK (IAN: 3-3-1K) (SEQ ID NO: 38), VPVETANVTMQLK (IAN: 2/3K) (SEQ ID NO: 44), VVPFQEVWGRSYK (IAN: 1-1-2K) (SEQ ID NO: 12) and GCCGDENLHK (IAN: 2-1-1K) (SEQ ID NO: 29).

"Multiple antigenic peptide systems" can also be used as immunization antigens [Tam, J. P. Proc Natl Acad Sci USA 1988, 85, 5409-5413]. In particular, 8-mers of IAN 1-1-1, IAN 3-3-1 or IAN 2/3 can be used:

IAN 1-1-1\8-mer: (SEQ ID NO: 67)

$(SAGNGSSEVEVV)_8K_4K_2K$-βA

IAN 3-3-1\8-mer: (SEQ ID NO: 68)

$(RSGDRPSYVELT)_8K_4K_2K$-βA

IAN 2/3\8-mer: (SEQ ID NO: 69)

$(VPVETANVTMQL)_8K_4K_2K$-βA

The selection of substances for the preparation of specific binding partners for the specific detection of gPIGF is explained in more detail below:

With the use of gPIGF, specific binding partners, in particular antibodies, are identified or prepared, for example by immunizations. These specific binding partners are distinguished in their characterization in that, during binding, interactions occur both with the PIGF and also with the bound binding partner.

For example, for the preparation of antibodies PIGF, which forms a complex with a binding partner, can be used in the immunization. In particular, these can be PIGF-1 homodimers which are complexed with sFlt-1. Corresponding complexes consisting of the relevant homologs, fragments, etc. can also be used.

The selection of substances for the preparation of specific binding partners for the specific detection of posttranslationally modified, in particular glycosylated PIGF is described in more detail below.

For this, PIGF or corresponding peptides with or without posttranslational modification are used for the preparation of specific binding partners, in particular antibodies. The specific binding partners are then suitable for specifically detecting the presence or absence of posttranslational modifications.

sequence or parts thereof are especially suitable as immunization antigens for the preparation of PlGF-3-specific antibodies:

IAN 6:
(SEQ ID NO: 52)
1   HVCRECR<u>HSP GRQSPDMPGD FRADAPSFLP PRRSLPMLFR MEWGCALTGS</u>

51  <u>OSAVWPSSPV PEEIPRMHPGR NGKKQQRKP</u> LREKMK

For example, N-glycosylated peptides which contain the sequence VETANVTMQ (IAN: 3-4) (SEQ ID NO: 39) or parts thereof, for example VETAN (IAN: 3-5) (SEQ ID NO: 40), TANVT (IAN: 3-6) (SEQ ID NO: 41) or NVTMQ (IAN: 3-7) (SEQ ID NO: 42), can be used for the preparation of specific binding partners, in particular antibodies, which can be used specifically for the detection of PlGF glycosylated on asparagine 84 (N 84). As well as these N-glycosylated peptides, it is also possible to use glycosylated PlGF, or corresponding fragments.

In addition, through the use of appropriate homologous, non-glycosylated peptides, PlGF and appropriate fragments, binding partners can be prepared which can be used in the specific detection of non-glycosylated PlGF.

The selection of substances for the preparation of specific binding partners for the specific detection of PlGF-2 is explained in more detail below:

Here, primary or secondary PlGF-2 isoforms, fragments thereof or corresponding peptides are used for the preparation of specific binding partners, in particular antibodies. Peptides and fragments thereof which contain the following sequence or parts thereof are especially suitable as immunization antigens for the preparation of PlGF-2-specific antibodies:

(SEQ ID NO: 48)
IAN 5:   REKMKPE<u>RR RPKGRGKRRR EKQRPTDCHL</u> CGDAVPR

Particularly preferably, peptides which contain the underlined sequence or parts thereof should be used.

Peptides which contain 5 consecutive amino acids of the sequence stated above (IAN 5) are particularly suitable, for example MKPER (IAN: 5-1) (SEQ ID NO: 49), KPERR (IAN: 5-2) (SEQ ID NO: 50), etc. down to LCGDA (IAN: 5-3) (SEQ ID NO: 51).

As well as the specific binding partners for PlGF-2, in particular antibodies, which are generated by immunization or other procedures with the proteins and peptides described above, it is also possible to use specific binding partners such as anionic compounds, in particular polyanionic compounds, preferably heparin compounds, in particular heparin sulfate proteoglycans. In a further embodiment, proteins which belong to the family of the semaphorin receptors, in particular neuropilins, preferably neuropilin-1 (NP-1) and neuropilin-2 (NP-2) are used as specific PlGF-2 binding partners.

Below, the selection of substances for the preparation of specific binding partners for the specific detection of PlGF-3 is described in more detail:

Here, primary or secondary PlGF-2 isoforms, fragments thereof or corresponding peptides are used for the preparation of specific binding partners, in particular antibodies. Peptides and fragments thereof which contain the following Particularly preferably, peptides which contain the underlined sequence or parts thereof should be used.

Peptides which contain 5 consecutive amino acids of the stated sequence IAN 6, i.e. for example CECRH (IAN: 6-1) (SEQ ID NO: 53), ECRHS (IAN: 6-2) (SEQ ID NO: 54) etc. down to KPLRE (IAN: 6-3) (SEQ ID NO: 55), are particularly suitable.

The selection of binding partners and of substances for the preparation of specific binding partners for the specific detection of PlGF-4 is described in more detail below:

Here, primary or secondary PlGF-4 isoforms, fragments thereof or corresponding peptides are used for the preparation of specific binding partners, in particular antibodies. Peptides and fragments thereof which contain the following sequence or parts thereof are especially suitable as immunization antigens for the preparation of PlGF-4-specific antibodies:

(SEQ ID NO: 56)
IAN 7:    NGKKQQ<u>RKPL</u> REKMKP<b>E</b>RRR PKGRG

Particularly preferably, peptides which contain the underlined amino acids should be used.

Peptides which contain the following sequences are especially suitable: QQRKP (IAN: 7-1) (SEQ ID NO: 57), QRKPL (IAN: 7-2) (SEQ ID NO: 58), RKPLR (IAN: 7-3) (SEQ ID NO: 59), KPLRE (IAN: 6-3) (SEQ ID NO: 55), MKPER (IAN: 5-1) (SEQ ID NO: 49), KPERR (IAN: 5-2) (SEQ ID NO: 50), PERRR (IAN: 7-4) (SEQ ID NO: 60) and ERRRP (IAN: 7-5) (SEQ ID NO: 61).

Since PlGF-4 contains both specific PlGF-2 sequences and also specific PlGF-3 sequences, the detection of PlGF-4 can be carried out by means of specific PlGF-2 binding partners and PlGF-3 binding partners according to the invention, in particular antibodies which are prepared by means of antigens according to the invention, in particular peptides.

The selection of binding partners and of substances for the preparation of specific binding partners for the specific detection of PlGF/VEGF heterodimers is described in more detail below:

Since PlGF/VEGF heterodimer contains both specific PlGF sequences (PlGF 1-4) and also specific VEGF sequences (VEGF isoforms), the detection of PlGF/VEGF hetero-dimers can be carried out by means of specific PlGF binding partners according to the invention, in particular antibodies, which are prepared by means of antigens according to the invention, in particular peptides, and VEGF antibodies.

In addition, according to the invention the VEGF/PlGF heterodimer-specific binding partner KDR/Flk-1, and isoforms, homologs, fragments and degradation products thereof may be used.

In particular, specific binding partners, especially antibodies, which were identified or prepared with the use of VEGF/PlGF heterodimers, for example by immunizations, and which during characterization show that during binding interactions both with the VEGF monomer and also with the PlGF monomer are entered into, can also be used.

A preferred process for the preparation of the peptides according to the invention, which inter alia are used as immunization antigens, is solid phase synthesis, wherein a multiple copy number of a peptide is synthesized on a lysine core [see also Tam J. P. (1988) Proc. Natl. Acad. Sci. USA 85: 5409-5413]. The peptide synthesis is preferably performed in accordance with a standard protocol by means of automatic machines, such as are for example supplied by Applied Biosystems (USA). Such multimeric peptides can moreover be bound to a carrier protein.

The specific binding partners according to the invention bind to an epitope. A "specific binding partner" should be understood to mean a member of a specific binding pair. The members of a specific binding pair are two molecules which each have at least one structure complementary to a structure of the other molecule, whereby the two molecules are capable of binding via a binding of the complementary structures. The term molecule also includes molecule complexes such as for example enzymes which consist of apo- and coenzyme, proteins which consist of several subunits, lipoproteins consisting of protein and lipids, etc. Specific binding partners can be naturally occurring but also substances prepared for example by chemical synthesis, microbiological techniques and/or genetic engineering processes. The following list serves for the illustration of the term specific binding partners, without however limiting this to these substances: thyroxine-binding globulin, steroid-binding proteins, antibodies, antibody fragments, designed repeat proteins, protein scaffolds, ankyrins, leucine-rich repeats, anticalins, duocalins, lipocalins, Affi-Bodies®, antigens, haptens, enzymes, lectins, nucleic acids, in particular aptamers, repressors, oligo- and polynucleotides, protein A, protein G, avidin, streptavidin, biotin, complement component C1q, nucleic acid-binding proteins, etc. Examples of specific binding pairs are: antibody-antigen, antibody-hapten, operator-repressor, nuclease-nucleotide, biotin-avidin, lectin-polysaccharide, steroid-steroid-binding protein, active substance-active substance receptor, hormone-hormone receptor, enzyme-substrate, IgG-protein A, complementary oligo- or polynucleotides, etc.

The term "peptide" in the sense of this invention includes acid amides which on hydrolysis decompose into amino acids, for example amino acid polymers such as for example polypeptides, oligopeptides, proteins or protein fragments.

The peptides according to the invention can be used as immunization antigens for the preparation of the antibodies according to the invention or also for affinity chromatographic purification of the antibodies according to the invention. Further, the peptides according to the invention can also be used in a process for the quantitative or qualitative detection of an analyte, preferably of the various PlGF forms. The peptides according to the invention can also be linked to a solid phase and/or a component of a signal-generating system, for example in an immunoassay.

The term "antigens" includes monovalent and polyvalent antigens. A polyvalent antigen is a molecule or a molecule complex onto which more than one immuno-globulin can simultaneously bind, while with a monovalent antigen only a single antibody can bind at the same time. A molecule which in itself alone is not immunogenic, but which is normally bound to a carrier for immunization purposes is usually described as a hapten.

The term "antibody" in the sense of this invention should be understood to mean an immunoglobulin, for example an immunoglobulin of the class or subclass IgA, IgD, IgE, IgG1, IgG2a, IgG2b, IgG3, IgG4 or IgM. An antibody has at least one binding site (often called a paratope) for one epitope (often also called an antigenic determinant) on an antigen or hapten. Such an epitope is for example characterized by its spatial structure and/or by the presence of polar and/or apolar groups. The binding site of the antibody is complementary to the epitope. The antigen-antibody reaction or the hapten-antibody reaction functions according to the so-called "lock and key" principle and is as a rule highly specific, i.e. the antibodies are capable of distinguishing small deviations in the primary structure, in the charge, in the spatial configuration and the steric arrangement of the antigen or hapten. In particular, the so-called "complementarity determining regions" of the antibody contribute to the binding of the antibody to the antigen or hapten.

The term "antibody" in the sense of this invention should however be understood to mean not only complete antibodies, but expressly also antibody fragments, such as for example Fab, Fv, F(ab')2, Fab'; and also chimeric, humanized, bi- or oligospecific, or "single chain" antibodies; and also aggregates, polymers and conjugates of immunoglobulins and/or fragments thereof, provided that the binding properties to the antigen or hapten are retained. Antibody fragments can for example be prepared by enzymatic cleavage of antibodies with enzymes such as pepsin or papain. Antibody aggregates, polymers and conjugates can be generated by a variety of methods, for example by heat treatment, reaction with substances such as glutaraldehyde, reaction with immunoglobulin-binding molecules, biotinylation of antibodies followed by reaction with streptavidin or avidin, etc.

An antibody in the sense of this invention can be a monoclonal or a polyclonal antibody. The antibody can be prepared by the usual process, for example by immunization of a human or an animal, such as for example mouse, rat, guinea pig, rabbit, horse, donkey, sheep, goat or chicken [see also Messerschmid (1996) BIOforum 11: 500-502], followed by isolation of the antiserum; or by establishing hybridoma cells followed by purification of the secreted antibody; or by cloning and expression of the nucleotide sequences or modified versions thereof, which encode the amino acid sequences which are responsible for the binding of the natural antibody to the antigen and/or hapten.

Antibodies according to the invention are in particular those antibodies which bind to the proteins, protein complexes or peptides described above.

Through the provision of the antibodies according to the invention it is now possible for the person skilled in the art, for example by competition experiments [see also Peters et al. (1985) Monoklonale Antikörper, Springer Verlag, Chapter 12.2 "Epitop-Analyse"], to identify other specific binding partners, antibodies expressly included therewith, which bind to the epitope of an antibody according to the invention. Thus specific binding partners can now be selected by means of phage display libraries, with synthetic peptide databases or by means of "recombinatorial antibody libraries" [Larrick & Fry (1991) Human Antibodies and Hybridomas 2: 172-189].

Also an object of this invention is an antibody according to the invention which is linked to a solid phase and/or a component of a signal-forming system.

The term "solid phase" in the sense of this invention includes an object which consists of porous and/or nonporous, as a rule water-insoluble material and which can take a great variety of forms, such as for example that of vessels, tubes, microtitration plates, spheres, microparticles, rods, strips, filter or chromatography paper, etc. As a rule the surface of the solid phase is hydrophilic or can be made hydrophilic. The solid phase can consist of a great variety of materials such as for example inorganic and/or organic materials, synthetic, naturally occurring and/or modified naturally occurring materials. Examples of solid phase materials are polymers, such as for example cellulose, nitrocellulose, cellulose acetate, polyvinyl chloride, polyacrylamide, crosslinked dextran molecules, agarose, polystyrene, polyethylene, polypropylene, poly-methacrylate or nylon; ceramics, glass, metals, in particular noble metals such as gold and silver; magnetite; mixtures or combinations of the same, etc. Cells, liposomes or phospholipid vesicles are also covered by the term solid phase.

The solid phase can have a coating of one or more layers, for example of proteins, carbohydrates, lipophilic substances, biopolymers, organic polymers or mixtures thereof, in order for example to suppress or prevent the nonspecific binding of sample components to the solid phase or for example to achieve improvements in the suspension stability of particulate solid phases, storage stability, dimensional stability or resistance to UV light, microbes or other destructively acting agencies.

Microparticles are often used as the solid phase and/or as labels. The term "microparticles" in the sense of this invention should be understood to mean particles which have an approximate diameter of at least 20 nm and not more than 20 µm, usually between 40 nm and 10 µm, preferably between 0.1 and 10 µm, particularly preferably between 0.1 and 5 µm, and quite especially preferably between 0.15 and 2 µm. The microparticles can be regularly or irregularly shaped. They can be balls, spheroids or balls with cavities of greater or lesser size. The microparticles can consist of organic or inorganic material or of a mixture or combination of both. They can consist of a porous or nonporous, swellable or nonswellable material. In principle, the microparticles can have any density, however particles with a density which is close to the density of water, such as about 0.7 to about 1.5 g/ml are preferred. The preferred microparticles are suspensible in aqueous solutions and suspension-stable for as long as possible. They may be transparent, partly transparent, or opaque. The microparticles can consist of several layers, such as for example the so-called "core-and-shell" particles with a core and one or more enclosing layers. The term microparticles for example includes dyestuff crystals, metal sols, silica particles, glass particles, magnetic particles, polymer particles, oil droplets, lipid particles, dextran and protein aggregates. Preferred microparticles are particles suspensible in aqueous solutions and consisting of water-insoluble polymeric material, in particular of substituted polyethylenes. Quite especially preferable are latex particles, for example of polystyrene, acrylic acid polymers, methacrylic acid polymers, acrylonitrile polymers, acrylonitrile-butadiene-styrene, polyvinyl acetate-acrylate, polyvinylpyridine or vinyl chloride-acrylate. Of particular interest are latex particles with reactive groups on their surface such as for example carboxyl, amino or aldehyde groups, which allow covalent binding for example of specific binding partners to the latex particles. The preparation of latex particles is for example described in EP 0 080 614, EP 0 227 054 and EP 0 246 446.

A "signal-generating system" can consist of one or more components, where at least one component is a detectable label. A label should be understood to mean any molecule which itself produces a signal or can induce the production of a signal, such as for example a fluorescent substance, a radioactive substance, an enzyme or a chemiluminescent substance. The signal can for example be detected or measured on the basis of enzyme activity, luminescence, light absorption, light scattering, emitted electromagnetic or radioactive radiation or a chemical reaction.

A label is capable of generating a detectable signal itself, so that no other components are necessary. Many organic molecules absorb ultraviolet and visible light, as a result of which these molecules can reach an excited energy state and emit the absorbed energy in the form of light of a wavelength other than that of the irradiation light. Again, other labels can create a detectable signal directly, for example radioactive isotopes or dyes.

Again, other labels require other components for signal creation, i.e. the signal-producing system in such a case includes all the components needed for generation of the signal, such as for example substrates, coenzymes, quenchers, accelerators, additional enzymes, substances which react with enzyme products, catalysts, activators, cofactors, inhibitors, ions, etc.

Examples of suitable labels are enzymes including horseradish peroxidase, alkaline phosphatase, glucose-6-phosphate dehydrogenase, alcohol dehydrogenase, glucose oxidase, β-galactosidase, luciferase, urease and acetylcholinesterase; dyes; fluorescent substances including fluorescein isothiocyanate, rhodamine, phyco-erythrin, phycocyanin, ethidium bromide, 5-dimethyl-aminonaphthalen-1-sulfonyl chloride and fluorescent chelates of rare earths; chemiluminescent substances including luminol, isoluminol, acridinium compounds, olefins, enol ethers, enamine, aryl vinyl ethers, dioxene, arylimidazole, lucigenin, luciferin and aequorin; sensitizers including eosin, 9,10-dibromoanthracene, methylene blue, porphyrin, phthalocyanine, chlorophyll, rose Bengal; coenzymes; enzyme substrates; radioactive isotopes including 125I, 131I, 14C, 3H, 32P, 33P, 35S, 51Cr, 59Fe, 57Co and 75Se; particles including magnetic particles or particles, preferably latex particles, which can themselves be labeled for example with dyes, sensitizers, fluorescent substances, chemi-luminescent substances, isotopes or other detectable labels; sol particles including gold or silver sols; liposomes or cells, which can themselves be labeled with detectable labels; etc. [see also EP-A2-0 515 194; U.S. Pat. No. 5,340,716; U.S. Pat. No. 5,545,834; Bailey et al. (1987) J. Pharmaceutical & Biomedical Analysis 5: 649-658].

A signal-generating system can also include components which can enter into a detectable interaction when in spatial proximity to one another, for example in the form of energy donors and energy acceptors such as for example photosensitizers and chemiluminescent substances (EP-A2-0 515 194), photosensitizers and fluorophores (WO 95/06877), radioactive iodine125 and fluorophores [Udenfriend et al. (1985) Proc. Natl. Acad. Sci. 82: 8672-8676], fluorophores and fluorophores [Mathis (1993) Clin. Chem. 39: 1953-1959] or fluorophores and fluorescence-quenchers (U.S. Pat. No. 3,996,345).

Interaction between the components includes the direct transfer of energy between the components, for example by light or electron radiation or via short-lived reactive chemical molecules. Also included therein are processes wherein the activity of one component is inhibited or intensified by one or more others, for example the inhibition or intensification of enzyme activity or the inhibition, intensification or modification (for example wavelength shift, polarization) of the electromagnetic radiation emitted by the component affected. Interaction between the components also includes enzyme cascades. In this case, the components are enzymes, whereof at least one provides the substrate for another, so that a maximal or minimal reaction rate of the coupled substrate conversion results.

An effective interaction between the components as a rule takes place when these are in spatial proximity, i.e. for example within a distance range of a few µm, in particular within a distance range of below 600 nm, preferably below 400 nm, quite especially preferably below 200 nm.

The term "associated" should be broadly understood and includes for example a covalent and a noncovalent bond, a direct and an indirect bond, adsorption onto a surface and inclusion into a depression or a cavity, etc. With a covalent bond, the antibodies or binding partners are bound to the solid phase or to the label via a chemical bond. Examples of a noncovalent bond are surface adsorption, inclusion into cavities or the binding of two specific binding partners. As well as direct bonding to the solid phase or the label, the antibodies or binding partners can also be bound to the solid phase or the label indirectly via specific interaction with other specific binding partners (see also EP-A2-0 411 945). Examples of this are: biotinylated antibodies which can be bound to the label via label-bound avidin or a fluorescein-antibody conjugate which can be bound to the solid phase via solid phase-bound anti-fluorescein antibody or an antibody which can be bound to the solid phase or the label via immunoglobulin-binding proteins.

A further object of this invention are antibodies or specific binding partners according to the invention which are used as in vitro diagnostic agents or as a component of an in vitro diagnostic agent.

With an in vitro diagnostic agent, the analyte to be detected, for example a particular PIGF form, is detected or the concentration or content thereof determined in a sample outside a living human or animal body.

A "sample" in the sense of the invention should be understood to mean the material which probably contains the substance to be detected (for examples of these, see EP-A2-0 515 194, "Analyt"). The term sample includes for example biological fluids or tissue in particular of man and animals, such as blood, plasma, serum, sputum, exudate, bronchoalveolar lavage, lymphatic fluid, synovial fluid, seminal fluid, vaginal mucus, feces, urine, cerebrospinal liquor, hair, skin, tissue samples or sections. Also included are cell culture samples, plant fluids or tissue, forensic samples, water and effluent samples, foodstuffs and medicaments. If necessary, the samples must be pretreated in order to make the analyte accessible to the detection method or in order to remove interfering sample components. Such pretreatment of samples may include the separation and/or lysis of cells, the precipitation, hydrolysis or denaturation of sample components such as for example proteins, centrifugation of samples, treatment of the sample with organic solvents such as for example alcohols, in particular methanol, or treatment of the sample with detergents. Commonly, the sample is transferred into another, most often aqueous, medium which should as far as possible not interfere with the detection process.

The antibodies according to the invention can be used in a process for the quantitative or qualitative determination of an analyte, preferably particular PIGF forms, in particular fPIGF, in a sample.

In a quantitative determination, the content, the concentration or the activity (for example enzyme activity) of the analyte in the sample is measured. The term "quantitative determination" also includes semi-quantitative methods which only ascertain the approximate content, concentration or activity of the analyte in the sample or can only be used to give a relative content, concentration or activity value. Qualitative determination should be understood to mean the detection of the presence of the analyte in the sample at all, or the demonstration that the concentration or activity of the analyte in the sample lies above or below a defined or several defined threshold values.

The invention thus also relates to methods for the quantitative or qualitative determination of an analyte, preferably particular PIGF forms, in particular fPIGF, in a sample and suitable reagents for this.

For the determination of analytes, binding tests are commonly used wherein a conclusion can be reached as to the presence, absence or content of the analyte in a sample by a specific binding of the analyte to be determined to analyte-specific binding partners. Immunoassays or also methods wherein oligo- or polynucleotides are hybridized are examples of binding tests.

The so-called "heterogenous binding tests" are characterized by one or more separation steps and/or washing steps. The separation can for example be effected by immune precipitation, precipitation with substances such as polyethylene glycol or ammonium sulfate, filtration, magnetic separation, or binding to a solid phase. With heterogenous binding tests in the sandwich format, as a rule one of the analyte-specific binding partners is bound to a solid phase and serves for the removal of the binding complex "analyte/analyte-specific binding partner" from the liquid phase, while the other analyte-specific binding partner bears a detectable label, for example an enzyme, a fluorescent or chemiluminescent label, etc., for the detection of the binding complex. These test methods are further subdivided into so-called one-step sandwich tests, wherein the two specific binding partners are simultaneously incubated with the sample, and two-step sandwich tests, wherein the sample is first incubated with the solid phase reagent and after a separation and washing step the solid phase-bound binding complex of analyte and analyte-specific binding partners is incubated with the detection reagent.

In "homogenous binding tests" no separation is effected between free components of the signal-generating system and those bound to the "analyte/analyte-specific binding partner" complex. The test mixture which contains the analyte-specific binding partner, the signal-generating components and the sample, is assayed after or even during the binding reaction without a further separation and/or washing step and the corresponding measurement signal is determined. Examples of homogenous immunoassays [see also Boguslaski & Li (1982) Applied Biochemistry and Biotechnology 7: 401-414] are turbidimetric or nephelometric methods, wherein the analyte-specific binding partners used for the determination can be linked to latex particles, such as for example EMIT® tests; CEDIA® tests; fluorescence-polarization immuno-assays; luminescent oxygen channeling immunoassays [LOCI®, see EP-A2-0 515 194; Ullman et al. (1994) Proc. Natl. Acad. Sci. 91: 5426-5430; Ullman et al. (1996) Clinical Chemistry 42: 1518-1526] etc. In a homogenous sandwich immunoassay, such as for example a nephelometric latex test, the antibody reagents are incubated together with the sample, and the measurement of the signal is performed during and/or after the incubation, without a separation or washing step being performed before the measurement. In other words: no separation of the antibody-bound analyte from the free analyte or from antibodies which have not bound to any analyte is carried out.

Homogenous and heterogenous binding tests can also be carried out in the form of a so-called "sandwich assay". In this, for example in a heterogenous binding test, the analyte is bound by one solid phase-associated, analyte-specific binding partner and one analyte-specific binding partner, which is linked to a component of a signal-generating system. In sandwich immunoassays, antibodies or antigens or haptens can constitute the analyte-specific binding partners.

A further specific embodiment of a heterogenous or homogenous binding test is the "indirect immunoassay". In this case, the analyte is an antibody. One of the analyte-specific binding partners is the antigen or for example a peptide according to the invention or a modified antigen of the antibody to be determined (=analyte), and the other analyte-specific binding partner is as a rule an immunoglobulin-binding protein such as for example an antibody, which can specifically bind to the antibodies to be determined (=analyte).

In a homogenous or heterogenous "competitive binding test" sample-analyte and reagent-analyte compete for binding to a limited number of analyte-specific binding partners. The reagent-analyte is for example a "modified analyte", such as for example a labeled or marked analyte, an analyte fragment such as for example the peptides according to the invention or an analyte analog. Examples for illustration of the principle: (i) sample-analyte competes with reagent-analyte, which is linked to a component of a signal-generating system, for binding to solid phase-linked, analyte-specific binding partners or (ii) sample-analyte competes with solid phase-linked analyte (=reagent-analyte) for binding to analyte-specific binding partners which are linked to a component of a signal-generating system.

The detection of different PIGF forms with the specific binding partners according to the invention, in particular antibodies, can also be effected by methods such as for example Western blot, dot blot, immuno electrophoresis, immunofixation electrophoresis, electroimmunodiffusion, immunoprecipitation, radial immunodiffusion, immunofixation, immunochromatography, latex agglutination, turbidimetric or nephelometric test, homogenous or heterogenous binding test, one or two-step test, sandwich test, indirect test, competitive test, "point-of-care" test, etc. These and other detection methods are for example described in "Labor and Diagnose", ed. L. Thomas, TH-Books Verlagsgesellschaft mbH, Frankfurt, 1998, Chapter 60 or in "Laboratory Techniques in Biochemistry and Molecular Biology—An Introduction to Radioimmunoassay and Related Techniques", ed. T. Chard, Elsevier, Amsterdam, 1987.

The term "point-of-care tests" or "POC tests" includes tests wherein no separate analytical or measuring instrument is needed for the implementation or assessment of the test. POC tests are in many cases based on immunochromatographic methods, immune complex separations by filtration and/or immunofixation techniques. The POC tests are particularly intended for measurements on site, for example at the sickbed or at home, for the emergency doctor and/or the private doctor and less for the large laboratory. POC tests can in particular also be performed by persons who do not have detailed medical and technical training and experience in the field of laboratory medicine. The term "POC tests" in the sense of this invention should also be understood to mean so-called home tests or OTC tests, which can be performed by medical laymen, such as for example the various pregnancy tests which are marketed for home use. Other POC tests for example relate to the detection of cardiac infarction markers, drugs, medicaments, and infection and inflammation markers. In many POC tests, specific binding partners are or in the course of the test become bound to or onto filter or chromatography strips. A positive or negative detection reaction can for example be coupled with the appearance or nonappearance of a colored band in a defined test field and/or the appearance or nonappearance of a certain symbol, for example the appearance or nonappearance of a "+" or a "−" and/or the intensity of the particular measurement signal.

A POC test for particular PIGF forms, in particular fPIGF, can for example be structured as follows: sample and labeled specific antibodies which can bind to the fPIGF form, but not or hardly at all to other PIGF forms, are applied onto a test strip. Examples of suitable labels are dyed latex particles, colloidal gold, enzymes etc. If the fPIGF form is contained in the sample, fPIGF/antibody complexes will form. These complexes move, for example by capillary forces, in the direction of a region wherein other specific binding partners, in particular antibodies, which can bind to other fPIGF epitopes and which are immobilized for example in the form of a band or become immobilized in the course of the test procedure (for example via a biotin-avidin bridge). The labeled fPIGF/antibody complexes become bound in this region and form a sandwich complex with the immobilized specific binding partners, in particular antibodies. The intensity of the label signal here is proportional to the fPIGF sample concentration. In a competitive POC test method, for example antibody fragments can be immobilized in a region of the test strip, or become immobilized in the course of the test procedure. This immobilized antibody would compete with the fPIGF form from the sample for binding to labeled anti-fPIGF antibodies. Alternatively, immobilized fPIGF antibodies and labeled fPIGF protein or the peptides according to the invention can also be used for the construction of a competitive fPIGF test.

A particularly preferable embodiment of the method according to the invention is a nephelometric or turbidimetric test, in particular such a test wherein antibodies according to the invention—preferably linked to microparticles (in particular to latex particles)—are used.

Another object according to the invention is a test kit which contains one or more of the antibodies and/or peptides according to the invention. Such a kit normally contains all or only some components of a test in packaged form. The antibodies and/or peptides according to the invention can for example be linked to one or more solid phases and/or one or more components of a signal-generating system. The test kit can for example contain standards, controls and other reagents, such as for example buffers, washing solutions, measurement signal-triggering solutions and/or enzyme substrate, cuvettes, pipettes and/or test directions. A particularly preferable test kit according to the invention contains antibodies according to the invention and/or peptides according to the invention linked to latex particles.

The antibodies and peptides according to the invention can also be used for affinity chromatography. The term "affinity chromatography" should be understood to mean a method for the purification and isolation of substances, in particular biopolymers, which is based on the fact that many substances can enter into a selective, noncovalent, reversible bond with binding partners specific to them. The principle of the method consists in that the specific binding partner is as a rule covalently bound to an insoluble matrix (for example porous glasses, or agarose, cellulose, dextran, polymer and silica gel-based gels) and placed in contact with a sample containing the substance. The test substance is immobilized and retained on account of its specific interaction with the matrix-bound specific binding partner, while all other substances contained in the sample are removed by elution. The test substance is then released from the matrix with a suitable elution agent which eliminates the noncovalent bonding between substance and specific binding partner (see also E. Buddecke, 1989, Grundrisse der Biochemie, Walter de Gruyter, Chapter 7 "Proteine").

A further object of this invention are antibodies or specific binding partners according to the invention which are used as therapeutic agents. This includes antibodies according to the invention or peptides according to the invention in a pharmaceutically compatible, sterile injection medium. A pharmaceutically compatible, sterile injection medium should for example be understood to mean a germ-free, pyrogen-free solution, for example saline or another electrolyte solution, such as is normally used for intravenous, intramuscular, intraperitoneal or subcutaneous administration of drugs, vaccines or contrast media.

A further object of this invention is the use of the antibodies according to the invention as diagnostic agents or as a component of a diagnostic agent.

A further object of this invention is a process for the preparation of an antibody according to the invention, which is characterized in that one or more of the peptides described above are used for the immunization.

The antibodies according to the invention can also be produced by the use of naturally occurring and/or recombinant PlGF and VEGF proteins, protein isoforms or fragments thereof.

A further object of the invention is the use of proteins, protein isoforms, fragments, degradation products, homologs, and peptides according to the invention as reference materials, standards, calibrators and controls. Reference materials are materials or substances which have properties which are established in such a manner that reference materials are used as calibrators, standards and controls. In addition, reference materials can be used for the validation of measurement methods and the assignment of defined values, in particular "conventionally correct values". The use of reference materials as calibrators, standards and controls or the use of calibrators, standards and controls which relate to reference materials or to the "conventional correct values" stated there is important in quality control and quality assurance.

The peptides used as the immunization antigen can be used for the immunization unbound and/or carrier-bound.

Typical carriers are for example proteins, such as for example ovalbumin, albumin or keyhole limpet hemocyanin (KLH), or polymers, such as for example polyethylene glycol, polyacrylamide or poly-d-glutamine-d-lysine. The peptides can for example be bound to these carriers by means of carbodiimide or glutaraldehyde or also by means of a heterobifunctional reagent, which can also act as a spacer, such as for example N-maleimido-butyryloxysuccinimide ester (GBMS). For other examples and coupling methods, see also Wong, S. (1993) Chemistry of Protein Conjugation and Cross-Linking, CRC Press, Inc., Boca Raton.

The immunization antigen can for example be dissolved in phosphate-buffered saline and treated with Immun Easy Mouse adjuvant. This emulsion can then be administered for example intradermally, intraperitoneally and/or subcutaneously to an animal, for example a rabbit, mouse, rat, guinea pig, horse, donkey, sheep, goat, chicken, etc. Booster injections, wherein the immunization antigen can also be emulsified with incomplete Freund adjuvant, can help to intensify the immune response.

Polyclonal antibodies according to the invention can be obtained from the antiserum of the immunized animals and can be further purified by affinity chromatography over a matrix, to which for example the relevant PlGF forms or the peptides used as the immunization antigen can be bound.

In order to create monoclonal antibodies according to the invention, the immune cells of immunized animals, such as for example of a mouse or rabbit, are fused with myeloma cells to create antibody-producing hybridoma cells and then suitable clones are isolated by the generally known procedure [see also Harlow & Lane (1988) Antibodies: A Laboratory Manual, Cold Spring Harbor Laboratory, Cold Spring Harbor; Peters et al. (1985) Monoklonale Antikörper: Herstellung and Charakterisierung, Springer Verlag]. The selection of the clones producing the desired monoclonal antibodies is carried out by means of specific screening methods. In these, the binding specificity of the antibodies released into the cell culture supernatant, for example to the immunization antigen or to some carrier of the immunization antigen, is checked by enzyme immunoassay, radioimmunoassay and/or western blotting. Hybridomas which produce antibodies according to the invention are reproduced by cloning. The hybridoma cell lines thus obtained are then available for the permanent production of monoclonal antibodies. Larger quantities of antibodies can for example be obtained from cell culture supernatant, in particular from fermenters or roller cultures and from ascites.

Depending on the desired use purpose, it is advantageous to use only parts of the antibodies, such as for example Fab-, F(ab')2-, or Fab'-fragments. These can for example be created by the enzymatic cleavage method known to the person skilled in the art [see also Harlow & Lane (1988) Antibodies: A Laboratory Manual, Cold Spring Harbor Laboratory, Cold Spring Harbor].

The antigen binding sites of an antibody are situated in the so-called variable domains, which are encoded by the V genes. Thus with the known genetic engineering methods [for example Sambrook et al. (1989) Molecular Cloning: A Laboratory Manual, Cold Spring Harbor Laboratory, Cold Spring Harbor, 2nd edition; McCafferty et al. (1990) Nature 348: 552-554] the corresponding nucleic acid sequence of an antibody according to the invention can also be determined and via this also the corresponding amino acid sequence, if this was not already known from amino acid sequencing. As the starting material for such analyses, the hybridoma cells or the antibody-producing immune cells of immunized animals can be used.

With the knowledge of the nucleic acid and/or amino acid sequence, it is then possible by means of standard genetic engineering and molecular biological methods [see also Johnson & Chiswell (1993) Current Opinion in Structural Biology 3: 564-571] to prepare humanized, chimeric, bi- or oligospecific antibodies, and also peptides derived from the "complementarity determining region" ("minimal recognition units"), single-chain fragments, and/or functional fusion products, for example recombinantly produced antibody-enzyme constructs [see also Larrick & Fry (1991) Human Antibodies and Hybridomas 2: 172-189; Kitano et al. (1986) Appl. Microbiol. Biotechnol. 24: 282-286; Thompson et al. (1986) J. Immunol. Methods 94: 7-12], which bind to the particular, specific epitopes of the PlGF forms, in particular to a peptide according to the invention. With such peptides included under the term "antibodies", for example a reduction in the immunogenicity and/or intensified activity on administration as a medicament or as an in vivo diagnostic agent can be achieved and/or advantages result for use as or in an in vitro diagnostic agent. The antibodies are also preparable, if necessary with recourse to genetic engineering methods, in fungi such as for example yeast cells [Fischer et al. (1999) Biol. Chem. 380: 825-839; Hiatt et al. (1992) Genetic Engineering 14: 49-64), plant, animal and prokaryotic cells (see also WO 95/25172) and isolated human cells.

A further object of this invention are also fungi, animal, plant or prokaryotic cells and isolated human cells which produce an antibody according to the invention. A preferred embodiment of this invention includes hybridoma cell lines which produce the antibodies according to the invention.

The examples described below serve for the illustration of individual aspects of this invention by way of example.

Example 1

Preparation of fPIGF-Specific Monoclonal Antibodies a) Immunization of Mice

BALB/c mice are each immunized intraperitoneally with 20 μg of immunization antigen (peptide with LRCTGC-CGDENLHCVPVET (IAN 2) (SEQ ID NO: 26) bound to KLH) in Immun Easy Mouse adjuvant (Qiagen GmbH, Germany). IAN 2 was synthesized by solid phase synthesis according to generally known methods. After 4 and 8 weeks, a booster injection with 20 μg each of immunization antigen without adjuvant was performed. In the last 3 days before the fusion, the mice were intravenously boosted with 10 μg of immunization antigen each.

b) Fusion

After sacrifice of the mice by $CO_2$ inhalation, the spleens are removed and single cell suspensions in serum-free Dulbecco's modified Eagle Medium (DMEM; PAN Biotech GmbH, Germany) are prepared. The cells are centrifuged (652×g) and washed twice in DMEM. Next the cell count is determined by Trypan blue staining. $2 \times 10^7$ myeloma cells (Sp2/0) are added for about $10^8$ spleen cells. After centrifugation (360×g) the supernatant is discarded, 1 ml of polyethylene glycol solution (PEG 4000, Merck Eurolab GmbH, Germany; ca. 50% in DMEM) is added to the cell pellet and incubated for 1 minute at 37° C. after resuspension. Next ca. 10 ml of DMEM are added, and the mixture incubated for 2 to 4 minutes at room temperature. The fused cells are centrifuged down (326×g) and the pellet is resuspended in DMEM+10% fetal calf serum (Bio Whittaker Europe, Belgium)+HAT medium (CC Pro GmbH, Germany) and filled into 24-well cell culture plates (Corning Costar GmbH, Germany). The approximate cell concentration is $5 \times 10^4$ to $5 \times 10^6$ cells per well.

After 2 to 3 weeks, the cell colonies formed (hybrids) are removed and transferred to new culture plates.

c) Screening

The specificity of the antibodies released into the cell culture is tested in a first test step by means of microtiter plates (Nunc GmbH & Co. KG, Germany) which are coated with a peptide with the amino acid sequence LRCTGC-CGDENLHCVPVET (SEQ ID NO: 26).

100 μl of cell culture supernatant (dilution 1:2) are pipetted into each well of the microtiter plate and incubated for 1 hour at +15 to +25° C. The plates are washed twice with washing solution POD (OSEW; Dade Behring Marburg GmbH, Germany) and then 100 μl of anti-mouse IgG/F (ab')2 POD conjugate (Dade Behring Marburg GmbH, Germany) are filled into each well and incubated for 1 hour at +15 to +25° C. After two further washings of the plate, 100 μl of Chromogen TMB-solution (Dade Behring Marburg GmbH, Germany) are filled into each well and incubated for a further 30 minutes at +15 to +25° C. After the incubation, 100 μl of stop solution POD (Dade Behring Marburg GmbH, Germany) are filled into each well and the microtiter plate is assessed at 450 nm on the BEP II (Behring-ELISA Processor II, Dade Behring Marburg GmbH, Germany).

In a second test step, the hybrids are tested again in the same test format after isolation as described above.

d) Cloning

Individual cells of hybrids which produce fPIGF-specific antibodies are cloned with a micromanipulator (Leitz Messtechnik GmbH, Germany). Culture supernatants of these clones are purified as described in g) and characterized in more detail as described in e), h) and i).

e) Determination of Antibody Class

The subclass of the antibodies against fPIGF is determined using the IsoStrip™ Mouse Monoclonal Antibody Isotyping Kit from Boehringer Mannheim Co., Germany.

f) Production of Antibodies

For the production of large quantities of antibodies, the relevant cell clones are transferred to roller bottles (Corning Costar GmbH, Germany) and expanded to the desired final volume at +37° C. Subsequently, the roller culture suspension is filtered through 0.22 μm to remove the cells. The now cell-free antibody solution is concentrated by Ultrafilter (separation limit 30,000 Dalton) and then purified.

g) Purification of the Antibodies

The antibody solution obtained is rebuffered with 0.14 M phosphate buffer pH 8.6 and applied onto a chromatography column filled with rProtein A Sepharose™ Fast Flow (Amersham Biosciences Europe GmbH, Germany) (1 ml of rProtein A Sepharose™ Fast Flow is used per 10 mg of antibody to be purified). All non-bound components are removed by washing the column with 0.14 M phosphate buffer pH 8.6. The bound antibody is eluted from the column with 0.1 M citric acid pH 3.0 and dialyzed against 0.05 M sodium acetate+0.5 M NaCl+0.05 M Tris+0.01% sodium azide pH 7.0.

h) Selection of Suitable Antibodies for an fPIGF Sandwich ELISA

The reaction of the monoclonal anti-fPIGF antibodies with the fPIGF-specific epitope (for example the peptide with the amino acid sequence LRCTGCCGDENLH-CVPVET (SEQ ID NO: 26)) is investigated:

Reaction with fPIGF:

As the solid phase, a microtiter plate which is coated with fPIGF is used. The anti-fPIGF antibodies from culture supernatants are incubated on this. After a washing step, binding of the antibody to the PIGF is detected via a conjugate consisting of polyclonal anti-mouse antibodies from the rabbit and the enzyme peroxidase with subsequent color reaction.

Reaction with an sFlt-1/PIGF Complex:

As the solid phase, a microtiter plate which is coated with fPIGF is used. sFlt-1 is incubated in this. The sFlt-1 which is used for this is "recombinant human VEGF R1 (Flt-1)/Fc Chimera" from R&D Systems (Catalog number: 321-FL or 321-FL/CF). After a washing step, anti-fPIGF antibodies from culture supernatants are incubated. After a washing step, no or only slight binding of specific anti-f PIGF antibodies will be detectable, since the binding sites are mainly occupied by sFlt-1. fPIGF-nonspecific antibodies also bind more to the sFlt-1/PIGF complex, i.e. gPIGF. After a washing step, binding of this nonspecific antibody is detected by a conjugate consisting of polyclonal anti-mouse antibodies from the rabbit and the enzyme peroxidase with subsequent color reaction.

In this test system, fPlGF-specific antibodies are those which show no or a markedly lesser color reaction in the reaction with an sFlt-1/PlGF complex than in the reaction with a fPlGF-specific peptide.

Accordingly, fPlGF-specific antibodies are selected. The suitability of these antibodies for use as solid phase antibodies in a sandwich ELISA with fPlGF-specific conjugate antibodies which is coupled to horseradish peroxidase by a procedure known to the person skilled in the art (for example Nakane conjugation) is investigated.

The suitability is checked in the sandwich ELISA as described in Example 2a). The essential decision criteria for suitability are a clear differentiation between fPlGF and sFlt-1/PlGF complex. Further criteria are the lower detection limit and the linearity of the calibration curve.

Example 2

Preparation of fPlGF-Specific Monoclonal Antibodies a) Immunization of Mice

BALB/c mice are each intraperitoneally immunized with 20 µg of immunization antigen (peptide with GCCGDEN-LHK (IAN 2-1-1K) (SEQ ID NO: 29) bound to KLH) in Immun Easy Mouse adjuvant (Qiagen GmbH, Germany). IAN 2-1-1K was synthesized by solid phase synthesis according to generally known methods. The purity of IAN 2-1-1K was checked by column chromatography (column: Merck 250×4 mm). For this, 0.1% TFA/water was used as buffer A, and 0.08% FFA/acetonitrile as buffer B. The flow rate was 0.8 ml. Detection was effected at 220 nm. Further, matrix-assisted laser desorption ionization mass spectrometry (MALDI-MS) was performed. The main peak was at 1075 m/z. After 4 and 8 weeks, a booster injection with 20 µg each of immunization antigen without adjuvant was performed. The last 3 days before the fusion, the mice are boosted with 10 µg each of immunization antigen.

The fusion b), cloning d), determination of antibody class e), production of antibodies f), purification of antibodies g) and selection of suitable antibodies for an fPlGF sandwich ELISA h) are performed as in Example 1. For the screening c), the same procedure as in Example 1 is also followed, with the exception that the specificity of the antibodies released into the cell culture is tested in a first test step by means of microtiter plates (Nunc GmbH & Co. KG, Germany) which are coated with a peptide with the amino acid sequence GCCGDENLHK (IAN: 2-1-1K) (SEQ ID NO: 29).

Example 3

Detection of fPlGF in a Sample a) Test Method A

Peroxidase-conjugated anti-PlGF antibodies are used in combination with a monoclonal anti-fPlGF antibody according to the invention in an enzyme immunoassay in accordance with the sandwich principle.

During the first incubation, the fPlGF contained in the sample—if present—binds to the antibodies according to the invention directed against fPlGF, which are immobilized on the surface of the wells of a microtitration plate. The wells are rinsed out and then peroxidase-conjugated anti-PlGF antibodies which are directed against any epitope—except for the receptor-binding epitope—of PlGF are used in a second binding reaction. With the aid of specific peroxidase-conjugated anti-PlGF antibodies, in principle the presence of particular PlGF isoforms can also be detected in this test method. For example, a PlGF-1-specific antibody can be used for the detection of PlGF-1, etc. In principle, the detection of the presence of different PlGF isoforms is possible with different specific antibodies. The excess enzyme-conjugated antibodies are washed off. Subsequently, the bound enzyme activity in the wells is determined. The enzymatic reaction of hydrogen peroxide and tetramethylbenzidine is stopped by addition of dilute sulfuric acid. The color intensity proportional to the fPlGF antigen concentration is determined photometrically at a wavelength of 450 nm and either qualitatively assessed by means of a cut-off or quantified on the basis of a calibration curve based on standards.

Such a sandwich immunoassay according to the invention detects fPlGF specifically in just one test procedure.

b) Test Method B

Peroxidase-conjugated, monoclonal anti-fPlGF antibodies according to the invention are used in combination with a monoclonal anti-fPlGF antibody according to the invention in an enzyme immunoassay according to the sandwich principle.

As in test method A, during the first incubation, the fPlGF contained in the sample—if present—binds to the antibodies according to the invention directed against fPlGF, which are immobilized on the surface of the wells of a microtitration plate. The wells are rinsed and then peroxidase-conjugated anti-fPlGF antibodies are used in a second binding reaction. The excess enzyme-conjugated antibodies are washed out. Next, the bound enzyme activity in the wells is determined. The enzymatic reaction of hydrogen peroxide and tetramethylbenzidine is stopped by addition of dilute sulfuric acid. The color intensity proportional to the fPlGF antigen concentration is determined photometrically at a wavelength of 450 nm and either qualitatively assessed by means of a cut-off or quantified on the basis of a calibration curve based on standards.

Such a sandwich immunoassay according to the invention detects fPlGF specifically in just one test procedure. Test method B is particularly preferred since fPlGF is generally present as a homodimer, for example as fPlGF-1 homodimer, and receptor can be bound at both poles of the homodimer. In test method B, an enzyme immunoassay according to the sandwich principle is used which utilizes one immobilized anti-fPlGF antibody and one peroxidase-conjugated anti-fPlGF antibody, so that fPlGF which has no binding partner at both poles is predominantly determined.

According to the examples and test methods described, the specificities of the other binding partners according to the invention, in particular of the antibodies, can also analogously be determined and used diagnostically.

Example 4

Preparation of Other fPlGF-Specific Monoclonal Antibodies

The following monoclonal antibodies were selected and investigated for their recognition of free and bound PlGF forms in accordance with Example 1. For the immunization, the immunization antigens stated in the following table were used. The antibody "MAB264" from R&D Systems is an antibody from the state of the art.

TABLE 1

| Monoclonal antibody | Immunization Antigen | Specificity |
|---|---|---|
| 05-54/04<br>05-64/026<br>05-81-05<br>05-81-010<br>(Group 1) | recombinant human PlGF;<br>R&D Systems, Catalog No. 264-PG/CF | free PlGF |
| 05-61/016<br>05-63/020<br>(Comparison antibodies) | recombinant human PlGF;<br>R&D Systems, Catalog No: 264-PG/CF | free and bound PlGF |
| 05-164/012<br>05-164/038<br>05-164/042<br>05-164/054<br>(Group 2) | IAN 3-3-1<br>(RSGDRPSYVELT)<br>(SEQ ID NO: 37) | free PlGF |
| 05-121/06<br>05-120/03<br>(Group 3) | IAN 1-1-2<br>(VVPFQEVWG RSY)<br>(SEQ ID NO: 11) | free PlGF |
| R&D Systems MAB264<br>(Comparison antibody, state of the art) | | free and bound PlGF |

The cell cultures which produce the monoclonal antibodies according to the invention stated in the table or which produce the comparison antibodies were deposited at the DSMZ (Deutsche Sammlung von Mikroorganismen and Zellkulturen GmbH), Mascheroder Weg 1b, 38124 Braunschweig, German Federal Republic, in accordance with the Budapest Treaty under the following entry numbers allocated by the international deposition office:

Cell culture 2005-81-05=DSM ACC2764
Cell culture 2005-81-010=DSM ACC2765
Cell culture 2005-64/026=DSM ACC2766
Cell culture 2005-63/020=DSM ACC2767
Cell culture 2005-61/016=DSM ACC2768
Cell culture 2005-54/04=DSM ACC2769
Cell culture 2005-164/054=DSM ACC2770
Cell culture 2005-164/042=DSM ACC2771
Cell culture 2005-164/038=DSM ACC2772
Cell culture 2005-164/012=DSM ACC2773
Cell culture 2005-121/06=DSM ACC2774
Cell culture 2005-120/03=DSM ACC2775

For all of the aforesaid cell cultures, the deposition date is 23 Mar. 2006.

Example 5

Reactivity of the Antibodies According to the Invention and the Comparison Antibodies with Recombinant (Free) PlGF Microtitration plates (Nunc, Type B), were coated with polyclonal antibody against mouse IgG/F(ab)2 (Dade Behring Marburg GmbH, Germany); coating concentration 10 µg/ml≈1.5 µg/well.

100 µl of the monoclonal antibodies to be investigated were pipetted into the wells of the microtitration plate at a concentration of a) 1.0 µg/ml or b) 0.1 µg/ml and incubated for 1 hour at +15 to +25° C. After washing of the microtitration plate three times with washing solution POD (Product No.: OSEW; Dade Behring Marburg, Germany) 100 µl of a solution of recombinant PlGF (R&D Systems, Catalog No.: 264-PG/CF) were added to each well at a concentration of 0.1 µg/ml and incubated for 1 hour at +15 to +25° C. After washing of the microtitration plate three times with washing solution POD, 100 µl of anti-human PlGF-POD conjugate (produced by a conventional conjugation method from "Human PlGF Affinity Purified Polyclonal Antibody", Prod. No.: AF-264-PB/R&D Systems) were filled into each well and incubated for 1 hour at +15 to +25° C. After a further washing of the microtitration plate three times, 100 µl of Chromogen TMB solution (Product No.: OUVF, Dade Behring Marburg GmbH, Germany) were filled into each well and incubated for a further 30 minutes at +15 to +25° C. After the incubation, 100 µl of stop solution POD (Product No.: OSFA, Dade Behring Marburg GmbH, Germany) were filled into each well and the microtitration plate was assessed at 450 nm on the BEP II (Dade Behring Marburg GmbH, Germany). The results are listed in Table 2.

TABLE 2

Determination of reactivity with PlGF by assessment of the microtitration plates at 450 nm on the BEP II.

| | Extinction at 450 nm | | | | | | | | | | | |
|---|---|---|---|---|---|---|---|---|---|---|---|---|
| | Antibody according to invention, Group 1 | | | | Antibody according to invention, Group 2 | | | | Antibody according to invention, Group 3 | Comparison antibody | | Antibody according to state of the art R&D |
| Antibody concentration [µg/ml] | 05-54/04 | 05-64/026 | 05-81-05 | 05-81-010 | 05-164/012 | 05-164/038 | 05-164/042 | 05-164/054 | 05-121/06 | 05-61/016 | 05-63/020 | Systems: MAB264 |
| 1.0 | 2.5 | 2.5 | 2.5 | 2.5 | 0.323 | 0.370 | 0.389 | 0.396 | 1.343 | 2.5 | 2.5 | 2.5 |
| 0.1 | 2.5 | 2.073 | 0.659 | 0.609 | 0.099 | 0.145 | 0.138 | 0.126 | 0.177 | 2.5 | 2.5 | 1.896 |

Example 6

Reactivity of the Antibodies According to the Invention, the Comparison Antibodies and the Antibodies from the State of the Art with PlGF/sFlt-1 Complex (gPlGF)

Microtitration plates (Nunc, Type B) were coated with polyclonal antibodies against human IgG/Fc (Dade Behring Marburg GmbH, Germany). Coating concentration 2.5 µl/ml≈0.376 µg/well.

100 µl of a solution of recombinant human VEGF R1 (Flt-1)/Fc chimera: R&D Systems, Catalog No.: 321-FL/CF) were placed in each well of the microtitration plate at a concentration of 1 µg/ml and incubated for 1 hour at +15 to +25° C. After washing of the microtitration plate three times with washing solution POD (see Example 5), for the preparation of the PlGF/sFlt-1 complex 100 µl of a solution of recombinant PlGF (see Example 5) was added to each well at a concentration of 1 µg/ml and incubated for 1 hour at +15 to +25° C. After washing of the microtitration plate three times with washing solution POD, 100 µl of the monoclonal antibody to be investigated were pipetted into each well at a concentration of a) 1 µg/ml or b) 0.1 µg/ml and incubated for 1 hour at +15 to +25° C. After washing of the microtitration plate three times with washing solution POD, 100 µl of anti-mouse IgG/F(ab)₂-POD conjugate (Dade Behring Marburg GmbH, Germany) were filled into each well and incubated for 1 hour at +15 to +25° C. After further washing of the microtitration plate three times, 100 µg of Chromogen TMB solution (see Example 5) were filled into each well and incubated for a further 30 minutes at +15 to +25° C. After the incubation, 100 µl of stop solution POD (see Example 5) were filled into each well and the microtitration plate was assessed at 450 nm on the BEP II (see Example 5). The results are listed in Table 3.

detection by chemiluminescence (Lumi-Imager, Roche Diagnostics)

Results: The two antibodies according to the invention 05-81-05 and 05-81-010 from Group 1 react with the following sequence segments:

1.  EKMKPERCGDAVP    (SEQ ID NO: 62)

2.  MKPERCGDAVPRR    (SEQ ID NO: 63)

The sequence recognized is identical with the C-terminal domain of PlGF-1.

Additional Tests with the Test Monoclonal Antibodies on the Solid Phase:

In the following Examples 8 and 9 only the higher affinity antibodies of Group 1 were tested in comparison to the state of the art and comparison antibodies.

TABLE 3

Determination of reactivity with PlGF/sFlt-1 complex by assessment of the microtitration plates at 450 nm on the BEP II.

| | Extinction at 450 nm | | | | | | | | | | | |
|---|---|---|---|---|---|---|---|---|---|---|---|---|
| Antibody | Antibody according to invention, Group 1 | | | | Antibody according to invention, Group 2 | | | | Antibody according to invention, Group 3 | Comparison antibody | | Antibody according to state of the art R&D |
| concentration [µg/ml] | 05-54/ 04 | 05-64/ 026 | 05-81- 05 | 05-81- 010 | 05-164- 012 | 05-164/ 038 | 05-164/ 042 | 05-164/ 054 | 05-121/ 06 | 05-61/ 016 | 05-63/ 020 | Systems: MAB264 |
| 1.0 | 0.036 | 0.032 | 0.043 | 0.045 | 0.027 | 0.026 | 0.029 | 0.023 | 0.028 | 2.500 | 2.500 | 0.691 |
| 0.1 | 0.035 | 0.028 | 0.026 | 0.026 | 0.022 | 0.023 | 0.023 | 0.023 | 0.028 | 0.692 | 0.750 | 0.217 |

The antibodies according to the invention show no reaction with the PlGF/sFlt-1 complex formed, whereas the comparison antibodies and the antibody from the state of the art show a clear reaction.

Example 7

Epitope Mapping

Scans of overlapping peptides which were derived from the sequence of human PlGF (13-meric peptides, 11 amino acids overlapping) were prepared by means of the SPOT synthesis technology. The methods are described in: Wenschuh, H. et al. (2000) "Coherent membrane supports for parallel microsynthesis and screening of bioactive peptides", *Biopolymers (Peptide Science)*, 55:188-206. The peptides were synthesized in defined order (as a "peptide array") stepwise on cellulose membranes, so that they were present covalently coupled to the cellulose membrane. Binding tests to assess the immunoreactivity of the peptides were performed directly on the arrays. The incubation protocol for this was as follows:
  equilibration in TBS buffer, pH 8.0
  2 hrs blocking buffer, pH 8.0
  2 hrs antibody incubation (3 µg/ml) in blocking buffer, pH 8.0
  washing with TBS (0.05% Tween20)
  2 hrs incubation with anti-mouse IgG-POD in blocking buffer, pH 8.0
  3×5 min washing with TBS (0.05% Tween20)

Example 8

Reaction with PlGF

Microtitration plates (see Example 5) were coated with the monoclonal antibodies according to the invention, with the comparison antibodies and with monoclonal antibodies from the state of the art. Coating concentration 3 µg/ml≈0.45 µg/well.

100 µl of a geometric dilution series starting with 50 ng/ml of recombinant PlGF (see Example 5) were pipetted into the wells of the microtitration plate and incubated for 1 hour at +15 to +25° C. After triple washing of the plate with washing solution POD (see Example 5), 100 µl of anti-human PlGF-POD conjugate (see Example 5) were filled into each well and incubated for 1.5 hours at +15 to +25° C. After further triple washing of the plate, 100 µl of Chromogen TMB solution (see Example 5) were filled into each well and incubated for a further 30 minutes at +15 to +25° C. After the incubation, 100 µl of stop solution POD (see Example 5) were filled into each well and the microtitration plate was assessed at 450 nm on the BEP II (see Example 5). The results are listed in Table 4.

TABLE 4

Determination of reactivity with PlGF by assessment of the microtitration plates at 450 nm on the BEP II

| | | Extinction at 450 nm | | | | | | Antibody according to state of the art R&D Systems: |
|---|---|---|---|---|---|---|---|---|
| Conc. | | Antibody according to invention, Group 1 | | | | Comparison antibody | | |
| [ng/ml] | | 05-54/04 | 05-64/026 | 05-81-05 | 05-81-010 | 5-61/016 | 06-63/020 | MAB264 |
| human recombinant PlGF | 50 | 2.500 | 2.500 | 1.603 | 2.074 | 2.500 | 2.500 | 2.500 |
| | 25 | 2.500 | 2.500 | 1.134 | 1.706 | 2.500 | 2.500 | 1.467 |
| | 12.5 | 2.500 | 1.926 | 0.610 | 1.154 | 2.500 | 2.500 | 0.885 |
| | 6.25 | 1.737 | 1.408 | 0.805 | 0.752 | 1.782 | 2.049 | 0.468 |
| | 3.13 | 1.144 | 0.819 | 0.394 | 0.413 | 1.165 | 1.330 | 0.232 |
| | 1.56 | 0.763 | 0.583 | 0.363 | 0.255 | 0.712 | 0.818 | 0.081 |
| | 0.78 | 0.406 | 0.376 | 0.234 | 0.143 | 0.414 | 0.456 | 0.050 |

Example 9

Reactivity of the Antibodies According to the Invention, the Comparison Antibodies and the Antibodies from the State of the Art with PlGF/sFlt-1 Complex (gPlGF)

Microtitration plates (see Example 5) were coated with the monoclonal antibodies according to the invention, with comparison antibodies and with monoclonal antibodies from the state of the art. Coating concentration 3 µg/ml≈0.45 µg/well.

In a reaction vessel, a geometric dilution series starting with 25 ng/ml of recombinant PlGF was prepared. Recombinant human VEGF R1 (Flt-1)/Fc chimera (see Example 6) at a concentration of 400 ng/ml was added to each dilution and incubated for 1 hour at +15 to +25° C. Next, 100 µl were pipetted into each of the wells of the microtitration plate and incubated for 1 hour at +15 to +25° C. After washing of the microtitration plate four times with washing solution POD (see Example 5), 100 µl of anti-human VEGF R1-POD conjugate (R&D Systems, Part 891096 from Quantikine Human VEGF R1 Immunoassay; DVR100B) were filled into each well and incubated for 1 hour at +15 to +25° C. After washing of the microtitration plate a further three times, 100 µl of Chromogen TMB solution (see Example 5) were filled into each well and incubated for a further 30 minutes at +15 to +25° C. After the incubation 100 µl of stop solution POD (see Example 5) were filled into each well and the microtitration plate was assessed at 450 nm on the BEP II (see Example 5). The results are listed in Table 5.

TABLE 5

Determination of reactivity with PlGF/sFlt-1 complex by assessment of the microtitration plates at 450 nm on the BEP II.

| | | Extinction at 450 nm | | | | | | Antibody according to state of the art R&D Systems: |
|---|---|---|---|---|---|---|---|---|
| Concentration [µg/ml] | | Antibody according to invention, Group 1 | | | | Comparison antibody | | |
| PlGF | VEGF R1 | 05-54/04 | 05-64/026 | 05-81-05 | 05-81-010 | 05-61/016 | 05-63/020 | MAB264 |
| 25 | 400 | 0.079 | 0.143 | 0.260 | 0.204 | 1.772 | 2.500 | 2.188 |
| 12.5 | 400 | 0.047 | 0.099 | 0.264 | 0.105 | 1.642 | 2.045 | 1.611 |
| 6.25 | 400 | 0.038 | 0.071 | 0.116 | 0.088 | 0.936 | 1.530 | 0.883 |
| 3.13 | 400 | 0.04 | 0.069 | 0.072 | 0.059 | 0.477 | 0.868 | 0.529 |
| 1.56 | 400 | 0.037 | 0.068 | 0.046 | 0.049 | 0.278 | 0.404 | 0.272 |
| 0.78 | 400 | 0.038 | 0.063 | 0.042 | 0.045 | 0.177 | 0.282 | 0.146 |
| 0.39 | 400 | 0.047 | 0.073 | 0.043 | 0.049 | 0.166 | 0.189 | 0.094 |

The antibodies according to the invention recognize the PlGF/sFlt-1 complex only very weakly or not at all. They are specific for free PlGF, while the comparison antibodies and the antibodies from the state of the art show clear reactions, i.e. are not specific for free PlGF.

The present invention is also expressly described by the following patent claims, without however restricting the invention thereto.

What is claimed is:

1. An isolated antibody, wherein the antibody is selected from the group consisting of
   monoclonal antibody 05-164/054, which is produced by a hybridoma cell line deposited under Deposit Accession No. DSM ACC2770,
   monoclonal antibody 05-164/042, which is produced by a hybridoma cell line deposited under Deposit Accession No. DSM ACC2771,
   monoclonal antibody 05-164/038, which is produced by a hybridoma cell line deposited under Deposit Accession No. DSM ACC2772, and
   monoclonal antibody 05-164/012, which is produced by a hybridoma cell line deposited under Deposit Accession No. DSM ACC2773.

2. A binding assay for detection of human Placental Growth Factor (PlGF) not bound by Flt-1 receptor (free PlGF) in a sample, comprising the steps of:
   (a) bringing the antibody of claim 1 into contact with the sample,
   (b) determining a binding complex comprising free PlGF from the sample and the antibody qualitatively or quantitatively.

3. A test kit for implementation of a binding assay for detection of human Placental Growth Factor (PlGF) not bound by Flt-1 receptor (free PlGF) in a sample, wherein the test kit comprises the antibody of claim 1 and reagents for detecting formation of a binding complex comprising free PlGF bound to the antibody.

4. An isolated antibody fragment of the antibody of claim 1, wherein the antibody fragment specifically binds to a peptide consisting of the amino acid sequence RSGDRPSYVELT (SEQ ID NO: 37).

5. A binding assay for detection of human Placental Growth Factor (PlGF) not bound by Flt-1 receptor (free PlGF) in a sample, comprising the steps of:
   (a) bringing the antibody fragment of claim 4 into contact with the sample,
   (b) determining a binding complex comprising free PlGF from the sample and the antibody fragment qualitatively or quantitatively.

6. A test kit for implementation of a binding assay for detection of human Placental Growth Factor (PlGF) not bound by Flt-1 receptor (free PlGF) in a sample, wherein the test kit comprises the antibody fragment of claim 4 and reagents for detecting formation of a binding complex comprising free PlGF bound to the antibody fragment.

7. An isolated hybridoma cell line, wherein the hybridoma cell line is selected from the group consisting of
   a hybridoma cell line deposited under Deposit Accession No. DSM ACC2770,
   a hybridoma cell line deposited under Deposit Accession No. DSM ACC2771,
   a hybridoma cell line deposited under Deposit Accession No. DSM ACC2772, and
   a hybridoma cell line deposited under Deposit Accession No. DSM ACC2773.

* * * * *

SEQUENCE LISTING

<160> NUMBER OF SEQ ID NOS: 69

<210> SEQ ID NO 1
<211> LENGTH: 149
<212> TYPE: PRT
<213> ORGANISM: Homo sapiens

<400> SEQUENCE: 1

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
            85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Cys Gly Asp
            130                 135                 140

Ala Val Pro Arg Arg
145

<210> SEQ ID NO 2
<211> LENGTH: 132
<212> TYPE: PRT
<213> ORGANISM: Homo sapiens

<400> SEQUENCE: 2

Ala Leu Pro Ala Val Pro Pro Gln Gln Trp Ala Leu Ser Ala Gly Asn
1               5                   10                  15

Gly Ser Ser Glu Val Glu Val Pro Phe Gln Glu Val Trp Gly Arg
            20                  25                  30

Ser Tyr Cys Arg Ala Leu Glu Arg Leu Val Asp Val Val Ser Glu Tyr
            35                  40                  45

Pro Ser Glu Val Glu His Met Phe Ser Pro Ser Cys Val Ser Leu Leu
    50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
            85                  90                  95

Arg Pro Ser Tyr Val Glu Leu Thr Phe Ser Gln His Val Arg Cys Glu
            100                 105                 110

Cys Arg Pro Leu Arg Glu Lys Met Lys Pro Glu Arg Cys Gly Asp Ala
            115                 120                 125

Val Pro Arg Arg
    130

<210> SEQ ID NO 3
<211> LENGTH: 132
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 3

Met Leu Pro Ala Val Pro Pro Gln Gln Trp Ala Leu Ser Ala Gly Asn
1               5                   10                  15

Gly Ser Ser Glu Val Glu Val Val Pro Phe Gln Glu Val Trp Gly Arg
            20                  25                  30

Ser Tyr Cys Arg Ala Leu Glu Arg Leu Val Asp Val Val Ser Glu Tyr
        35                  40                  45

Pro Ser Glu Val Glu His Met Phe Ser Pro Ser Cys Val Ser Leu Leu
    50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
                85                  90                  95

Arg Pro Ser Tyr Val Glu Leu Thr Phe Ser Gln His Val Arg Cys Glu
            100                 105                 110

Cys Arg Pro Leu Arg Glu Lys Met Lys Pro Glu Arg Cys Gly Asp Ala
        115                 120                 125

Val Pro Arg Arg
    130

<210> SEQ ID NO 4
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Leu Pro Ala Val Pro Pro Gln Gln Trp Ala Leu Ser Ala Gly Asn
1               5                   10                  15

Gly Ser Ser Glu Val Glu Val Val Pro Phe Gln Glu Val Trp Gly Arg
            20                  25                  30

Ser Tyr Cys Arg Ala Leu Glu Arg Leu Val Asp Val Val Ser Glu Tyr
        35                  40                  45

Pro Ser Glu Val Glu His Met Phe Ser Pro Ser Cys Val Ser Leu Leu
    50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
                85                  90                  95

Arg Pro Ser Tyr Val Glu Leu Thr Phe Ser Gln His Val Arg Cys Glu
            100                 105                 110

Cys Arg Pro Leu Arg Glu Lys Met Lys Pro Glu Arg Arg Pro Lys
        115                 120                 125

Gly Arg Gly Lys Arg Arg Glu Lys Gln Arg Pro Thr Asp Cys His
    130                 135                 140

Leu Cys Gly Asp Ala Val Pro Arg Arg
145                 150

<210> SEQ ID NO 5
<211> LENGTH: 204
<212> TYPE: PRT

<213> ORGANISM: Homo sapiens

<400> SEQUENCE: 5

```
Ala Leu Pro Ala Val Pro Pro Gln Gln Trp Ala Leu Ser Ala Gly Asn
1               5                   10                  15

Gly Ser Ser Glu Val Glu Val Val Pro Phe Gln Glu Val Trp Gly Arg
            20                  25                  30

Ser Tyr Cys Arg Ala Leu Glu Arg Leu Val Asp Val Val Ser Glu Tyr
        35                  40                  45

Pro Ser Glu Val Glu His Met Phe Ser Pro Ser Cys Val Ser Leu Leu
    50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
                85                  90                  95

Arg Pro Ser Tyr Val Glu Leu Thr Phe Ser Gln His Val Arg Cys Glu
            100                 105                 110

Cys Arg His Ser Pro Gly Arg Gln Ser Pro Asp Met Pro Gly Asp Phe
        115                 120                 125

Arg Ala Asp Ala Pro Ser Phe Leu Pro Pro Arg Arg Ser Leu Pro Met
    130                 135                 140

Leu Phe Arg Met Glu Trp Gly Cys Ala Leu Thr Gly Ser Gln Ser Ala
145                 150                 155                 160

Val Trp Pro Ser Ser Pro Val Pro Glu Glu Ile Pro Arg Met His Pro
                165                 170                 175

Gly Arg Asn Gly Lys Lys Gln Gln Arg Lys Pro Leu Arg Glu Lys Met
            180                 185                 190

Lys Pro Glu Arg Cys Gly Asp Ala Val Pro Arg Arg
            195                 200
```

<210> SEQ ID NO 6
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Ala Leu Pro Ala Val Pro Pro Gln Gln Trp Ala Leu Ser Ala Gly Asn
1               5                   10                  15

Gly Ser Ser Glu Val Glu Val Val Pro Phe Gln Glu Val Trp Gly Arg
            20                  25                  30

Ser Tyr Cys Arg Ala Leu Glu Arg Leu Val Asp Val Val Ser Glu Tyr
        35                  40                  45

Pro Ser Glu Val Glu His Met Phe Ser Pro Ser Cys Val Ser Leu Leu
    50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
                85                  90                  95

Arg Pro Ser Tyr Val Glu Leu Thr Phe Ser Gln His Val Arg Cys Glu
            100                 105                 110

Cys Arg His Ser Pro Gly Arg Gln Ser Pro Asp Met Pro Gly Asp Phe
        115                 120                 125

Arg Ala Asp Ala Pro Ser Phe Leu Pro Pro Arg Arg Ser Leu Pro Met
```

```
                130                 135                 140
Leu Phe Arg Met Glu Trp Gly Cys Ala Leu Thr Gly Ser Gln Ser Ala
145                 150                 155                 160

Val Trp Pro Ser Ser Pro Val Pro Glu Glu Ile Pro Arg Met His Pro
                165                 170                 175

Gly Arg Asn Gly Lys Lys Gln Gln Arg Lys Pro Leu Arg Glu Lys Met
            180                 185                 190

Lys Pro Glu Arg Arg Pro Lys Gly Arg Gly Lys Arg Arg Arg Glu
        195                 200                 205

Lys Gln Arg Pro Thr Asp Cys His Leu Cys Gly Asp Ala Val Pro Arg
    210                 215                 220

Arg
225

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Gly Asn Gly Ser Ser Glu Val Glu Val Val Pro Phe Gln Glu
1               5                   10                  15

Val Trp Gly Arg Ser Tyr Cys Arg Ala Leu Glu Arg Leu Val
            20                  25                  30

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Gln Glu Val Trp Gly Arg Ser Tyr
1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Gly Asn Gly Ser Ser Glu Val Glu Val Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Gly Asn Gly Ser Ser Glu Val Glu Val Val Lys
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Val Val Pro Phe Gln Glu Val Trp Gly Arg Ser Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Val Val Pro Phe Gln Glu Val Trp Gly Arg Ser Tyr Lys
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Glu Val Val Pro Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Val Val Pro Phe Gln
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Val Pro Phe Gln Glu
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 16

Pro Phe Gln Glu Val
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Gln Glu Val Trp
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Glu Val Trp Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Trp Gly Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Trp Gly Arg Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Gly Arg Ser Tyr
1               5

<210> SEQ ID NO 22
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 22

Gly Arg Ser Tyr Cys
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Tyr Cys Arg
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Tyr Cys Arg Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Cys Arg Ala Leu
1               5

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Arg Cys Thr Gly Cys Cys Gly Asp Glu Asn Leu His Cys Val Pro
1               5                   10                  15

Val Glu Thr

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

-continued

```
Gly Asp Glu Asn Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Cys Cys Gly Asp Glu Asn Leu His
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Cys Cys Gly Asp Glu Asn Leu His Lys
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Cys Cys Gly Asp
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Cys Gly Asp Glu
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Gly Asp Glu Asn
1               5

<210> SEQ ID NO 33
<211> LENGTH: 29
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 33

Val Glu Thr Ala Asn Val Thr Met Gln Leu Leu Lys Ile Arg Ser Gly
1               5                   10                  15

Asp Arg Pro Ser Tyr Val Glu Leu Thr Phe Ser Gln His
            20                  25

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Leu Leu Lys Ile Arg Ser Gly Asp Arg Pro Ser Tyr
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Leu Leu Lys Ile
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Pro Ser Tyr Val
1               5

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Gly Asp Arg Pro Ser Tyr Val Glu Leu Thr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Gly Asp Arg Pro Ser Tyr Val Glu Leu Thr Lys
```

```
<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Glu Thr Ala Asn Val Thr Met Gln
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Glu Thr Ala Asn
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ala Asn Val Thr
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Val Thr Met Gln
1               5

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Pro Val Glu Thr Ala Asn Val Thr Met Gln Leu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 44

Val Pro Val Glu Thr Ala Asn Val Thr Met Gln Leu Lys
1               5                   10

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Ser Gln His Val Arg Cys Glu Cys Arg Pro Leu Arg Glu Lys
1               5                   10                  15

Met Lys Pro Glu
            20

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Cys Arg Pro
1

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Leu Arg Glu Lys
1               5

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Glu Lys Met Lys Pro Glu Arg Arg Pro Lys Gly Arg Gly Lys
1               5                   10                  15

Arg Arg Arg Glu Lys Gln Arg Pro Thr Asp Cys His Leu Cys Gly Asp
            20                  25                  30

Ala Val Pro Arg
        35

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Met Lys Pro Glu Arg
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Pro Glu Arg Arg
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Cys Gly Asp Ala
1               5

<210> SEQ ID NO 52
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Val Arg Cys Glu Cys Arg His Ser Pro Gly Arg Gln Ser Pro Asp
1               5                   10                  15

Met Pro Gly Asp Phe Arg Ala Asp Ala Pro Ser Phe Leu Pro Pro Arg
            20                  25                  30

Arg Ser Leu Pro Met Leu Phe Arg Met Glu Trp Gly Cys Ala Leu Thr
        35                  40                  45

Gly Ser Gln Ser Ala Val Trp Pro Ser Ser Pro Val Pro Glu Glu Ile
    50                  55                  60

Pro Arg Met His Pro Gly Arg Asn Gly Lys Lys Gln Gln Arg Lys Pro
65                  70                  75                  80

Leu Arg Glu Lys Met Lys
                85

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Glu Cys Arg His
1               5

```
<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Cys Arg His Ser
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Pro Leu Arg Glu
1               5

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Gly Lys Lys Gln Gln Arg Lys Pro Leu Arg Glu Lys Met Lys Pro
1               5                   10                  15

Glu Arg Arg Arg Pro Lys Gly Arg Gly
            20                  25

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Arg Lys Pro
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Arg Lys Pro Leu
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 59

Arg Lys Pro Leu Arg
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Glu Arg Arg Arg
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Arg Arg Arg Pro
1               5

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Lys Met Lys Pro Glu Arg Cys Gly Asp Ala Val Pro
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Lys Pro Glu Arg Cys Gly Asp Ala Val Pro Arg Arg
1               5                   10

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Arg Arg Pro Lys Gly Arg Gly Lys Arg Arg Glu Lys Gln Arg
1               5                   10                  15

Pro Thr Asp Cys His Leu
            20

<210> SEQ ID NO 65
<211> LENGTH: 72
<212> TYPE: PRT
<213> ORGANISM: Homo sapiens

<400> SEQUENCE: 65

His Ser Pro Gly Arg Gln Ser Pro Asp Met Pro Gly Asp Phe Arg Ala
1               5                   10                  15

Asp Ala Pro Ser Phe Leu Pro Pro Arg Arg Ser Leu Pro Met Leu Phe
            20                  25                  30

Arg Met Glu Trp Gly Cys Ala Leu Thr Gly Ser Gln Ser Ala Val Trp
        35                  40                  45

Pro Ser Ser Pro Val Pro Glu Glu Ile Pro Arg Met His Pro Gly Arg
    50                  55                  60

Asn Gly Lys Lys Gln Gln Arg Lys
65                  70

<210> SEQ ID NO 66
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Phe Ser Gln His Val Arg Cys Glu Cys Arg Pro Leu Arg Glu Lys
1               5                   10                  15

Met Lys Pro Glu Arg Cys Gly Asp Ala Val Pro Arg Arg
            20                  25

<210> SEQ ID NO 67
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Ala Gly Asn Gly Ser Ser Glu Val Glu Val Val Ser Ala Gly Asn
1               5                   10                  15

Gly Ser Ser Glu Val Glu Val Val Ser Ala Gly Asn Gly Ser Ser Glu
            20                  25                  30

Val Glu Val Val Ser Ala Gly Asn Gly Ser Ser Glu Val Glu Val Val
        35                  40                  45

Ser Ala Gly Asn Gly Ser Ser Glu Val Glu Val Val Ser Ala Gly Asn
    50                  55                  60

Gly Ser Ser Glu Val Glu Val Val Ser Ala Gly Asn Gly Ser Ser Glu
65                  70                  75                  80

Val Glu Val Val Ser Ala Gly Asn Gly Ser Ser Glu Val Glu Val Val
                85                  90                  95

Lys Lys Lys Lys Lys Lys Lys
            100

<210> SEQ ID NO 68
<211> LENGTH: 103
<212> TYPE: PRT
<213> ORGANISM: Artificial Sequence
<220> FEATURE:

-continued

```
<223> OTHER INFORMATION: Description of Artificial Sequence: Synthetic
      polypeptide

<400> SEQUENCE: 68

Arg Ser Gly Asp Arg Pro Ser Tyr Val Glu Leu Thr Arg Ser Gly Asp
1               5                   10                  15

Arg Pro Ser Tyr Val Glu Leu Thr Arg Ser Gly Asp Arg Pro Ser Tyr
            20                  25                  30

Val Glu Leu Thr Arg Ser Gly Asp Arg Pro Ser Tyr Val Glu Leu Thr
        35                  40                  45

Arg Ser Gly Asp Arg Pro Ser Tyr Val Glu Leu Thr Arg Ser Gly Asp
    50                  55                  60

Arg Pro Ser Tyr Val Glu Leu Thr Arg Ser Gly Asp Arg Pro Ser Tyr
65                  70                  75                  80

Val Glu Leu Thr Arg Ser Gly Asp Arg Pro Ser Tyr Val Glu Leu Thr
                85                  90                  95

Lys Lys Lys Lys Lys Lys Lys
            100

<210> SEQ ID NO 69
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Val Pro Val Glu Thr Ala Asn Val Thr Met Gln Leu Val Pro Val Glu
1               5                   10                  15

Thr Ala Asn Val Thr Met Gln Leu Val Pro Val Glu Thr Ala Asn Val
            20                  25                  30

Thr Met Gln Leu Val Pro Val Glu Thr Ala Asn Val Thr Met Gln Leu
        35                  40                  45

Val Pro Val Glu Thr Ala Asn Val Thr Met Gln Leu Val Pro Val Glu
    50                  55                  60

Thr Ala Asn Val Thr Met Gln Leu Val Pro Val Glu Thr Ala Asn Val
65                  70                  75                  80

Thr Met Gln Leu Val Pro Val Glu Thr Ala Asn Val Thr Met Gln Leu
                85                  90                  95

Lys Lys Lys Lys Lys Lys Lys
            100
```